United States Patent
Jones et al.

(10) Patent No.: US 12,138,605 B2
(45) Date of Patent: Nov. 12, 2024

(54) FLUID MIXING SYSTEMS WITH MODULAR IMPELLERS AND RELATED METHODS

(71) Applicant: Life Technologies Corporation, Carlsbad, CA (US)

(72) Inventors: Nephi D. Jones, Newton, UT (US); Jason D. Brown, Logan, UT (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 517 days.

(21) Appl. No.: 17/165,564

(22) Filed: Feb. 2, 2021

(65) Prior Publication Data
US 2021/0237009 A1 Aug. 5, 2021

Related U.S. Application Data

(60) Provisional application No. 62/969,339, filed on Feb. 3, 2020.

(51) Int. Cl.
*B01F 7/00* (2006.01)
*B01F 7/22* (2006.01)
(Continued)

(52) U.S. Cl.
CPC ......... *B01F 27/191* (2022.01); *B01F 27/071* (2022.01); *B01F 27/0722* (2022.01);
(Continued)

(58) Field of Classification Search
CPC ............................. B01F 27/191; B01F 27/071
See application file for complete search history.

(56) References Cited

U.S. PATENT DOCUMENTS

| 1,011,259 A | 12/1911 | Smith et al. |
| 3,322,401 A | 5/1967 | Mersch |

(Continued)

FOREIGN PATENT DOCUMENTS

| DE | 202009005407 U1 | 9/2009 |
| DE | 102008058338 A1 | 5/2010 |

(Continued)

OTHER PUBLICATIONS

SPXFlow, R135 Impeller, (site visited Sep. 21, 2023), spxflow.com website, URL :<https://www.spxflow.com/lightnin/products/r135-impeller/> (Year: 2023). 2 pages.

*Primary Examiner* — Elizabeth Insler
(74) *Attorney, Agent, or Firm* — Mintz Levin Cohn Ferris Glovsky and Popeo, P.C.

(57) ABSTRACT

A mixing system for mixing a liquid includes a first impeller segment having a first mount and a first mixing blade secured to the first mount and a second impeller segment having a second mount and a first mixing blade secured to the second mount, the second impeller segment being separate and discrete from the first impeller segment. One or more drive members are secured to the first impeller segment and the second impeller segment for concurrently rotating the first impeller segment and the second impeller segment about a rotational axis. The first impeller segment and the second impeller segment are secured to the one or more drive members so that a plane extending normal to the axis of rotation intersects with the first mixing blade of the first impeller segment and the first mixing blade of the second impeller segment.

19 Claims, 31 Drawing Sheets

(51) Int. Cl.
  *B01F 15/00*   (2006.01)
  *B01F 27/07*   (2022.01)
  *B01F 27/072*  (2022.01)
  *B01F 27/113*  (2022.01)
  *B01F 27/191*  (2022.01)
  *B01F 27/91*   (2022.01)
  *B01F 35/513*  (2022.01)
  *C12M 1/06*    (2006.01)
  *B01F 101/44*  (2022.01)

(52) U.S. Cl.
  CPC .......... *B01F 27/074* (2022.01); *B01F 27/113* (2022.01); *B01F 27/91* (2022.01); *B01F 35/513* (2022.01); *C12M 27/02* (2013.01); *B01F 2101/44* (2022.01)

(56) References Cited

U.S. PATENT DOCUMENTS

| | | | |
|---|---|---|---|
| 3,559,962 A | 2/1971 | Enssle et al. | |
| 3,692,427 A | 9/1972 | Risse | |
| 4,083,653 A | 4/1978 | Stiffler | |
| 4,549,103 A | 10/1985 | Shiga | |
| 4,601,583 A * | 7/1986 | Amorese | B01F 27/071 366/330.1 |
| 4,722,608 A | 2/1988 | Salzman et al. | |
| 4,779,990 A | 10/1988 | Hjort et al. | |
| 5,885,001 A | 3/1999 | Thomas | |
| 5,941,636 A | 8/1999 | Lu | |
| 6,082,890 A * | 7/2000 | Heinzmann | B01F 27/113 366/330.4 |
| 6,083,587 A | 7/2000 | Smith et al. | |
| 6,190,033 B1 | 2/2001 | Rickman et al. | |
| 6,334,705 B1 | 1/2002 | Weetman | |
| D468,009 S | 12/2002 | Hoenderkamp et al. | |
| 6,572,262 B1 | 6/2003 | Russel-Smith | |
| 6,670,171 B2 | 12/2003 | Carll | |
| D506,823 S | 6/2005 | Chiu et al. | |
| 7,114,844 B2 | 10/2006 | Weetman | |
| D561,888 S | 2/2008 | Yang et al. | |
| 7,384,783 B2 | 6/2008 | Kunas et al. | |
| D576,186 S | 9/2008 | Rosso et al. | |
| 7,441,940 B2 | 10/2008 | Vanek | |
| 7,487,688 B2 | 2/2009 | Goodwin | |
| 7,682,067 B2 | 3/2010 | West et al. | |
| 7,878,099 B2 | 2/2011 | Loibl | |
| 7,879,599 B2 | 2/2011 | Goodwin et al. | |
| 7,887,230 B2 * | 2/2011 | Rosso | B01F 27/0723 366/331 |
| D664,262 S | 7/2012 | Khan | |
| 8,455,242 B2 | 6/2013 | Staheli et al. | |
| 8,485,716 B2 | 7/2013 | Handa | |
| 8,506,198 B2 | 8/2013 | West et al. | |
| 8,603,805 B2 | 12/2013 | Goodwin et al. | |
| 8,641,314 B2 | 2/2014 | Thacker et al. | |
| D744,018 S | 11/2015 | Sugiura | |
| 9,248,420 B2 | 2/2016 | Rawlings | |
| 9,839,886 B2 | 12/2017 | Staheli et al. | |
| 9,855,537 B2 | 1/2018 | Williams | |
| 9,968,896 B1 | 5/2018 | Himmelsbach et al. | |
| 10,022,683 B2 | 7/2018 | Multner et al. | |
| 10,335,751 B2 | 7/2019 | Williams | |
| D865,822 S | 11/2019 | Murray | |
| D927,931 S | 8/2021 | Kuchinski et al. | |
| D996,287 S | 8/2023 | Nussbaumer et al. | |
| 2002/0105856 A1 | 8/2002 | Terentiev | |
| 2002/0131654 A1 | 9/2002 | Smith et al. | |
| 2003/0077466 A1 | 4/2003 | Smith et al. | |
| 2003/0131654 A1 | 7/2003 | Robertson et al. | |
| 2003/0161216 A1 | 8/2003 | Gigas et al. | |
| 2006/0240546 A1 | 10/2006 | Goodwin et al. | |
| 2006/0270036 A1 | 11/2006 | Goodwin et al. | |
| 2006/0280028 A1 | 12/2006 | West et al. | |
| 2008/0130406 A1 | 6/2008 | Rosso et al. | |
| 2010/0260010 A1 | 10/2010 | Jorntz | |
| 2011/0013473 A1 | 1/2011 | Ludwig | |
| 2011/0026360 A1 | 2/2011 | Greller et al. | |
| 2011/0188928 A1 | 8/2011 | West et al. | |
| 2011/0229963 A1 | 9/2011 | Fatherazi et al. | |
| 2011/0310696 A1 | 12/2011 | Goodwin et al. | |
| 2013/0101982 A1 | 4/2013 | Goodwin et al. | |
| 2013/0136617 A1 | 5/2013 | Wang et al. | |
| 2014/0071788 A1 | 3/2014 | Wang et al. | |
| 2014/0106453 A1 | 4/2014 | Kunas et al. | |
| 2015/0044057 A1 | 2/2015 | Dinnison | |
| 2015/0117142 A1 * | 4/2015 | Staheli | B01F 27/191 366/279 |
| 2017/0183617 A1 | 6/2017 | Jones et al. | |
| 2019/0217261 A1 | 7/2019 | Jones et al. | |

FOREIGN PATENT DOCUMENTS

| | | |
|---|---|---|
| FR | 782935 | 9/1934 |
| JP | H06285353 A | 10/1994 |
| WO | 2011/139209 A1 | 11/2011 |
| WO | 2013/151733 A1 | 10/2013 |

* cited by examiner

FLUID MIXING SYSTEMS WITH MODULAR IMPELLERS AND RELATED METHODS

CROSS-REFERENCE TO RELATED APPLICATIONS

This application claims the benefit of U.S. Provisional Application No. 62/969,339, filed Feb. 3, 2020, which is incorporated herein by specific reference.

BACKGROUND OF THE DISCLOSURE

1. The Field of the Disclosure

The present disclosure relates to fluid mixing systems, such as bioreactors or fermentors, that incorporate modular impellers and related systems.

2. The Relevant Technology

The biopharmaceutical industry uses a broad range of mixing systems for a variety of processes such as in the preparation of media and buffers and in the growing, mixing and suspension of cells and microorganisms. Some conventional mixing systems, including bioreactors and fermentors, comprise a flexible bag disposed within a rigid support housing. An impeller is disposed within the flexible bag and is coupled with a drive shaft projecting into the bag. Rotation of the drive shaft and impeller facilitates mixing and/or suspension of the fluid contained within flexible bag.

One particular challenge of growing cells or microorganisms within a bioreactor or fermentor is that the culture must be continuously and uniformly mixed to ensure proper growth of the culture but the mixing force must not be so great as to damage the cells or microorganisms. In one approach to improve mixing efficiently, i.e., improve mixing per unit of power applied, impellers are used having parabolic blades. For example, impellers are produced having a central hub to receive a drive shaft and six parabolic blades that radially outwardly project around the hub.

Although impellers having parabolic blades generally improve mixing efficiency relative to conventional impellers, such impellers also have significant shortcomings. Most notably, impellers having parabolic blades are difficult to produce and are particularly difficult to mass produce. Conventional impellers have relatively simple shapes. As such, molds can be produced that enable the impellers to be easily mass produced by injection molding using a polymer. In contrast, impellers with parabolic blades have very complex geometries that would make it difficult, in not impossible, to produce a mold for injection molding the impellers. As such, impellers having parabolic blades are typically manufactured from metal where the six individual blades are all welded to a common hub. Such processing is expensive and time consuming and thus prohibitive to mass production. Although such impellers can be produced by printing, the printing of such complex impellers is also expensive and time consuming.

Accordingly, what is needed in the art are improved fluid mixing systems with impellers that overcome one or more of the above shortcomings and/or that otherwise improve mixing efficiency.

SUMMARY OF THE DISCLOSURE

Various independent aspects and examples consistent with the present teaching are set out in the following numbered clauses:

Clause 1: A mixing system for mixing a liquid, comprising:
  a first impeller segment comprising a first mount and a first mixing blade secured to the first mount;
  a second impeller segment comprising a second mount and a first mixing blade secured to the second mount, the second impeller segment being separate and discrete from the first impeller segment; and
  means secured to the first impeller segment and the second impeller segment for concurrently rotating the first impeller segment and the second impeller segment about a rotational axis,
  wherein the first impeller segment and the second impeller segment are secured to the means for concurrently rotating so that a plane extending normal to the rotational axis intersects with the first mixing blade of the first impeller segment and the first mixing blade of the second impeller segment.

Clause 2: The mixing system as recited in clause 1, further comprising a second mixing blade secured to the first mount and being spaced apart from the first mixing blade of the first mount.

Clause 3: The mixing system as recited in clause 2, wherein the first mixing blade and the second mixing blade are the only mixing blades secured to first mount of the first impeller segment.

Clause 4: The mixing system as recited in any preceding clause, wherein the first impeller segment and the second impeller segment have identical configurations.

Clause 5: The mixing system as recited in any preceding clause, wherein the first mount has an opening extending therethrough and the second mount has an opening extending therethrough, the opening of the first mount and the opening of the second mount being aligned.

Clause 6: The mixing system as recited in clause 5, wherein the rotational axis passes through the opening of the first mount and the opening of the second mount.

Clause 7: The mixing system as recited in clause 5 or 6, wherein the opening of the first mount is polygonal.

Clause 8: The mixing system as recited in any preceding clause, wherein the first mount has a top face and an opposing bottom face and the second mount has a top face and an opposing bottom face, the bottom face of the first mount being disposed directly against or directly adjacent to the top face of the second mount.

Clause 9: The mixing system as recited in any preceding clause, wherein the first mount and the second mount are disposed at different locations along the rotational axis.

Clause 10: The mixing system as recited in any preceding clause, wherein the plane extending normal to the rotational axis does not intersect with both the first mount and the second mount.

Clause 11: The mixing system as recited in clause 2, wherein the first mount comprises:
  a hub having an opening extending therethrough;
  a first arm projecting from the hub, the first mixing blade projecting from the first arm; and
  a second arm projecting from the hub, the second mixing blade projecting from the second arm.

Clause 12: The mixing system as recited in any preceding clause, wherein the first mixing blade of the first impeller segment has a front face with a concave or parabolic configuration.

Clause 13: The mixing system as recited in any preceding clause, wherein the first mount has a top surface and an opposing bottom surface that extend to an outer perimeter edge, the first mixing blade of the first impeller segment outwardly projecting from the outer perimeter edge of the first mount.

Clause 14: The mixing system as recited in any preceding clause, wherein the first mixing blade of the first impeller segment further comprises a front face and an opposing back face, the front face having a length that extends from a first terminal end to an opposing second terminal end and having a width that extends between an inside edge connected to the first mount and an opposing outside edge.

Clause 15: The mixing system as recited in clause 14, wherein at least a portion of the front face the first mixing blade of the first impeller segment extends linearly between the inside edge and the opposing outside edge.

Clause 16: The mixing system as recited in clause 14 or 15, wherein at least a portion of the front face the first mixing blade of the first impeller segment extends in a curve between the first terminal end and the opposing second terminal end.

Clause 17: The mixing system as recited in clause 16, wherein the curve of the front face of the first mixing blade of the first impeller segment has an apex that extends along the width between the inside edge and the outside edge.

Clause 18: The mixing system as recited in clause 17, wherein first mixing blade of the first impeller segment comprises:
a first wing having a length extending from the apex to the first terminal end; and
a second wing having a length extending from the apex to the second terminal end, the length of the first wing being greater than or equal to the length of the second wing.

Clause 19: The mixing system as recited in any preceding clause, further comprising a third impeller segment secured to the means for concurrently rotating, the third impeller segment comprising a third mount and a first mixing blade secured to the third mount, the third impeller segment being separate and discrete from the first impeller segment and the second impeller segment.

Clause 20: The mixing system as recited in clause 19, wherein the first impeller segment, the second impeller segment, and the third impeller segment all have identical configurations.

Clause 21: The mixing system as recited in clause 19, wherein the first mixing blade of the third impeller segment has a different configuration from the first mixing blade of the first impeller segment.

Clause 22: The mixing system as recited in any preceding clause, further comprising means for securing the first impeller segment to the second impeller segment.

Clause 23: The mixing system as recited in clause 22, wherein the means for securing comprises a mechanical connection securing the first impeller segment to the second impeller segment.

Clause 24: The mixing system as recited in any preceding clause, wherein the means for concurrently rotating comprises a first drive member coupled to the first impeller segment and the second impeller segment.

Clause 25: The mixing system as recited in clause 24, wherein the first mount of the first impeller segment and the second mount of the second impeller segment each have an opening extending therethrough, the first drive member being disposed within the opening of the first mount and the second mount.

Clause 26: The mixing system as recited in clause 24 or 25, wherein the first drive member is tubular, a drive shaft being removably received within the first drive member.

Clause 27: The mixing system as recited in any preceding clause, wherein the means for concurrently rotating comprises a first drive member secured to the second impeller segment and a second drive member secured to the second impeller segment.

Clause 28: The mixing system as recited in clause 27, wherein the first drive member and the second drive member are secured on opposing ends of the second impeller segment so that the first drive member and the second drive member are laterally spaced apart.

Clause 29: The mixing system as recited in clause 27 or 28, wherein the first drive member and the second drive member are only secured to the first impeller segment through the second impeller segment.

Clause 30: The mixing system as recited in clause 27, 28, or 29, wherein the first drive member and the second drive member each comprise a flexible drive line having a longitudinal axis, the first drive member and the second drive member being sufficiently flexible that they can be twisted under torsion about their longitudinal axis over an angle of at least 90°, 180°, 270° or 360° without plastic deformation.

Clause 31: The mixing system as recited in any preceding clause, further comprising a container having a compartment, the first impeller segment and the second impeller segment being disposed within the compartment.

Clause 32: The mixing system as recited in clause 31, wherein the container comprises a collapsible, flexible bag being comprised of one or more sheets of polymeric film.

Clause 33: The mixing system as recited in clause 31 or 32, further comprising a biological culture comprised of cells or microorganisms disposed within the compartment of the container.

Clause 34: A mixing system for mixing a liquid, comprising:
a first impeller segment comprising a first mount, a first mixing blade secured to the first mount, and a second mixing blade secured to the first mount, the first mixing blade being spaced apart from second mixing blade;
a second impeller segment comprising a second mount and a first mixing blade secured to the second mount, the second impeller segment being separate and discrete from the first impeller segment; and
an elongated first drive member, the first impeller segment and the second impeller segment being secured to the first drive member so that a plane intersects with the first mixing blade and the second mixing blade of the first impeller segment and also with the first mixing blade of the second impeller segment.

Clause 35: The mixing system as recited in clause 34, wherein the first mount, the first mixing blade and the second mixing blade are integrally formed as a single unitary structure.

Clause 36: The mixing system as recited in clause 34 or 35, further comprising a second mixing blade secured to the second mount and being spaced apart from the first mixing blade of the second mount.

Clause 37: The mixing system as recited in any one of clauses 34-36, wherein the first impeller segment and the second impeller segment have identical configurations.

Clause 38: The mixing system as recited in any one of clauses 34-37, wherein the first mount has an opening extending therethrough and the second mount has an opening extending therethrough, the opening of the first mount and the opening of the second mount being aligned.

Clause 39: The mixing system as recited in clause 38, wherein a rotational axis of the first drive member passes through the opening of the first mount and the opening of the second mount.

Clause 40: The mixing system as recited in any one of clauses 34-39, wherein the first mount has a top face and an opposing bottom face and the second mount has a top face and an opposing bottom face, the bottom face of the first mount being disposed directly against or directly adjacent to the top face of the second mount.

Clause 41: The mixing system as recited in any one of clauses 34-40, wherein the first mount and the second mount are disposed at different locations along a length of the first drive member.

Clause 42: The mixing system as recited in any one of clauses 34-41, wherein the plane extends normal to a rotational axis of the first drive member and does not intersect with both the first mount and the second mount.

Clause 43: The mixing system as recited in any one of clauses 34-42, wherein the first mount comprises:
  a hub having an opening extending therethrough;
  a first arm projecting from the hub, the first mixing blade projecting from the first arm; and
  a second arm projecting from the hub, the second mixing blade projecting from the second arm.

Clause 44: The mixing system as recited in any one of clauses 34-43, wherein the first mixing blade of the first impeller segment has a front face with a concave or parabolic configuration.

Clause 45: The mixing system as recited in any one of clauses 34-44, further comprising a third impeller segment secured to the first drive member, the third impeller segment comprising a third mount and a first mixing blade secured to the third mount, the third impeller segment being separate and discrete from the first impeller segment and the second impeller segment.

Clause 46: The mixing system as recited in any one of clauses 34-45, further comprising means for securing the first impeller segment to the second impeller segment.

Clause 47: The mixing system as recited in any one of clauses 34-46, wherein the first drive member is tubular, a drive shaft being removably received within the first drive member.

Clause 48: The mixing system as recited in any one of clauses 34-46, further comprising an elongated second drive member secured to the first impeller segment and the second impeller segment.

Clause 49: The mixing system as recited in clause 48, wherein the first drive member and the second drive member are secured directly on opposing ends of the second impeller segment so that the first drive member and the second drive member are laterally spaced apart.

Clause 50: The mixing system as recited in clause 48 or 49, wherein the first drive member and the second drive member are only secured to the first impeller segment through the second impeller segment.

Clause 51: The mixing system as recited in clause 48, 49, or 50, wherein the first drive member and the second drive member each comprise a flexible drive line having a longitudinal axis, the first drive member and the second drive member being sufficiently flexible that they can be twisted under torsion about their longitudinal axis over an angle of at least 90°, 180°, 270° or 360° without plastic deformation.

Clause 52: The mixing system as recited in any one of clauses 34-51, further comprising a container having a compartment, the first impeller segment and the second impeller segment being disposed within the compartment.

Clause 53: The mixing system as recited in clause 52, wherein the container comprises a collapsible, flexible bag being comprised of one or more sheets of polymeric film.

Clause 54: The mixing system as recited in clause 52 or 53, further comprising a biological culture comprised of cells or microorganisms disposed within the compartment of the container.

Clause 55: A mixing system for mixing a liquid, comprising:
  a first impeller segment comprising a first mount and only two mixing blades or only one mixing blade being secured to the first mount;
  a second impeller segment comprising a second mount and only two mixing blades or only one mixing blade being secured to the second mount, the second impeller segment being separate and discrete from the first impeller segment;
  an elongated first drive member secured to the first impeller segment and/or the second impeller segment; and
  a collapsible, flexible bag having a compartment and being comprised of one or more sheets of polymeric film, the first impeller segment, the second impeller segment and at least a portion of the elongated first drive member being disposed within the compartment of the flexible bag.

Clause 56: The mixing system as recited in any one of clause 55, wherein the first impeller segment and the second impeller segment have identical configurations.

Clause 57: The mixing system as recited in clause 55 or 56, wherein the first mount has an opening extending therethrough and the second mount has an opening extending therethrough, the opening of the first mount and the opening of the second mount being aligned.

Clause 58: The mixing system as recited in clause 57, wherein a rotational axis of the first drive member passes through the opening of the first mount and the opening of the second mount.

Clause 59: The mixing system as recited in any one of clauses 55-58, wherein the first mount has a top face and an opposing bottom face and the second mount has a top face and an opposing bottom face, the bottom face of the first mount being disposed directly against or directly adjacent to the top face of the second mount.

Clause 60: The mixing system as recited in any one of clauses 55-59, wherein the first mount and the second mount are disposed at different locations along a length of the first drive member.

Clause 61: The mixing system as recited in any one of clauses 55-60, further comprising a third impeller segment secured to the first drive member, the third impeller segment comprising a third mount and only two mixing blades or only one mixing blade being secured to the third mount, the third impeller segment being separate and discrete from the first impeller segment and the second impeller segment.

Clause 62: The mixing system as recited in any one of clauses 55-61, further comprising means for securing the first impeller segment to the second impeller segment.

Clause 63: The mixing system as recited in any one of clauses 55-62, wherein the first drive member is tubular.

Clause 64: The mixing system as recited in any one of clauses 55-62, further comprising an elongated second drive member secured to the first impeller segment and/or the second impeller segment.

Clause 65: The mixing system as recited in clause 64, wherein the first drive member and the second drive member are secured directly on opposing ends of the second impeller segment so that the first drive member and the second drive member are laterally spaced apart.

Clause 66: The mixing system as recited in clauses 64 or 65, wherein the first drive member and the second drive member are only secured to the first impeller segment through the second impeller segment.

Clause 67: The mixing system as recited in clauses 64, 65, or 66, wherein the first drive member and the second drive member each comprise a flexible drive line having a longitudinal axis, the first drive member and the second drive member being sufficiently flexible that they can be twisted under torsion about their longitudinal axis over an angle of at least 90°, 180°, 270° or 360° without plastic deformation.

Clause 68: The mixing system as recited in any one of clauses 55-67, further comprising a biological culture comprised of cells or microorganisms disposed within the compartment of the flexible bag.

Clause 69: A method for assembling a mixing system for mixing a liquid, comprising:
  securing a first impeller segment and a second impeller segment to an elongated first drive member, the first drive member having a rotational axis during operation, the first impeller segment comprising a first mount and a first mixing blade secured to the first mount, the second impeller segment comprising a second mount and a first mixing blade secured to the second mount, the second impeller segment being separate and discrete from the first impeller segment, a plane extending normal to the rotational axis of the first drive member intersecting with the first mixing blade of the first impeller segment and the first mixing blade of the second impeller segment; and
  sealing the first impeller segment and the second impeller segment within a compartment of a collapsible, flexible bag being comprised of one or more sheets of polymeric film.

Clause 70: The method as recited in clause 69, wherein the step of securing a first impeller segment and a second impeller segment comprises sliding the first drive member through an opening in the first mount of the first impeller segment and then through an opening in the second mount of the second impeller segment.

Clause 71: The method as recited in clause 70, further comprising sliding the first drive member through an opening in a third mount of a third impeller segment, a first mixing blade being secured to the third mount.

Clause 72: The method as recited in clause 71, wherein each of the first impeller segment, the second impeller segment and the third impeller segment include the first mixing blade and a spaced apart second mixing blade.

Clause 73: The method as recited in clause 69, wherein the step of securing the first impeller segment and the second impeller segment comprises:
  securing together the first impeller segment and the second impeller segment without use of the first drive member; and
  securing the first drive member directly to the second impeller segment.

Clause 74: The method as recited in clause 73, further comprising securing a second drive member directly to the second impeller segment at a location spaced apart from the first drive member.

Clause 75: The method as recited in clause 74, wherein the first drive member and the second drive member each comprise a flexible drive line having a longitudinal axis, the first drive member and the second drive member being sufficiently flexible that they can be twisted under torsion about their longitudinal axis over an angle of at least 90°, 180°, 270° or 360° without plastic deformation.

Clause 76: A method for assembling a mixing system for mixing a liquid, comprising:
  securing a first impeller segment to a second impeller segment, the first impeller segment comprising a first mount and a first mixing blade secured to the first mount, the second impeller segment comprising a second mount and a first mixing blade secured to the second mount, the second impeller segment being separate and discrete from the first impeller segment; and
  attaching the second impeller segment secured to the first impeller segment to an elongated first drive member.

Clause 77: The method as recited in clause 76, wherein the step of attaching the second impeller segment to the elongated first drive member comprises sliding the first drive member through an opening in the first mount of the first impeller segment and through an opening in the second mount of the second impeller segment.

Clause 78: The method as recited in clause 76, further comprising securing an elongated second drive member directly to the second impeller segment at a location spaced apart from the first drive member.

Clause 79: The method as recited in clause 78, wherein the first drive member and the second drive member each comprise a flexible drive line having a longitudinal axis, the first drive member and the second drive member being sufficiently flexible that they can be twisted under torsion about their longitudinal axis over an angle of at least 90°, 180°, 270° or 360° without plastic deformation.

Clause 80: A mixing system for mixing a liquid, comprising:
  a first impeller segment comprising a first mount and a first mixing blade secured to the first mount, the first mixing blade comprising a front face and an opposing back face, the front face having a length that extends from a first terminal end to an opposing second terminal end and having a width that extends between an inside edge connected to the first mount and an opposing outside edge; and
  a second impeller segment comprising a second mount and a first mixing blade secured to the second mount, the second impeller segment being separate and discrete from the first impeller segment.

Clause 81: The mixing system as recited in clause 14 or 80, wherein the first terminal end of the first mixing blade has a thickness extending between the front face and the opposing back face, the thickness of the first terminal end varying at points along the width of the first terminal end.

Clause 82: The mixing system as recited in clause 81, wherein the first terminal end has a first thickness at an intersection between the first terminal end and the outside edge and has a second thickness at a center point between the inside edge and the outside edge, the first thickness being greater than the second thickness.

Clause 83: The mixing system as recited in clause 1, 34, 55, or 80 further comprising:
  the first mount having a first hole formed thereon; and
  the second mount having a first post projecting therefrom, the first post being received within the first hole so as to secure the first mount to the second mount.

Clause 84: The mixing system as recited in clause 83, wherein the first post is secured within the first hole by frictional engagement.

Each of the above independent aspects of the disclosure may include any of the features, options and possibilities set out in this document, including those under the other independent aspects, and may also include any combination of any of the features, options and possibilities set out in this document.

BRIEF DESCRIPTION OF THE DRAWINGS

To further clarify the above and other advantages and features of the present disclosure, a more particular description of the disclosure will be rendered by reference to specific embodiments thereof which are illustrated in the appended drawings. It is appreciated that these drawings depict only illustrated embodiments of the disclosure and are therefore not to be considered limiting of its scope. The disclosure will be described and explained with additional specificity and detail through the use of the accompanying drawings in which.

DETAILED DESCRIPTION OF THE PREFERRED EMBODIMENTS

Figure 1:
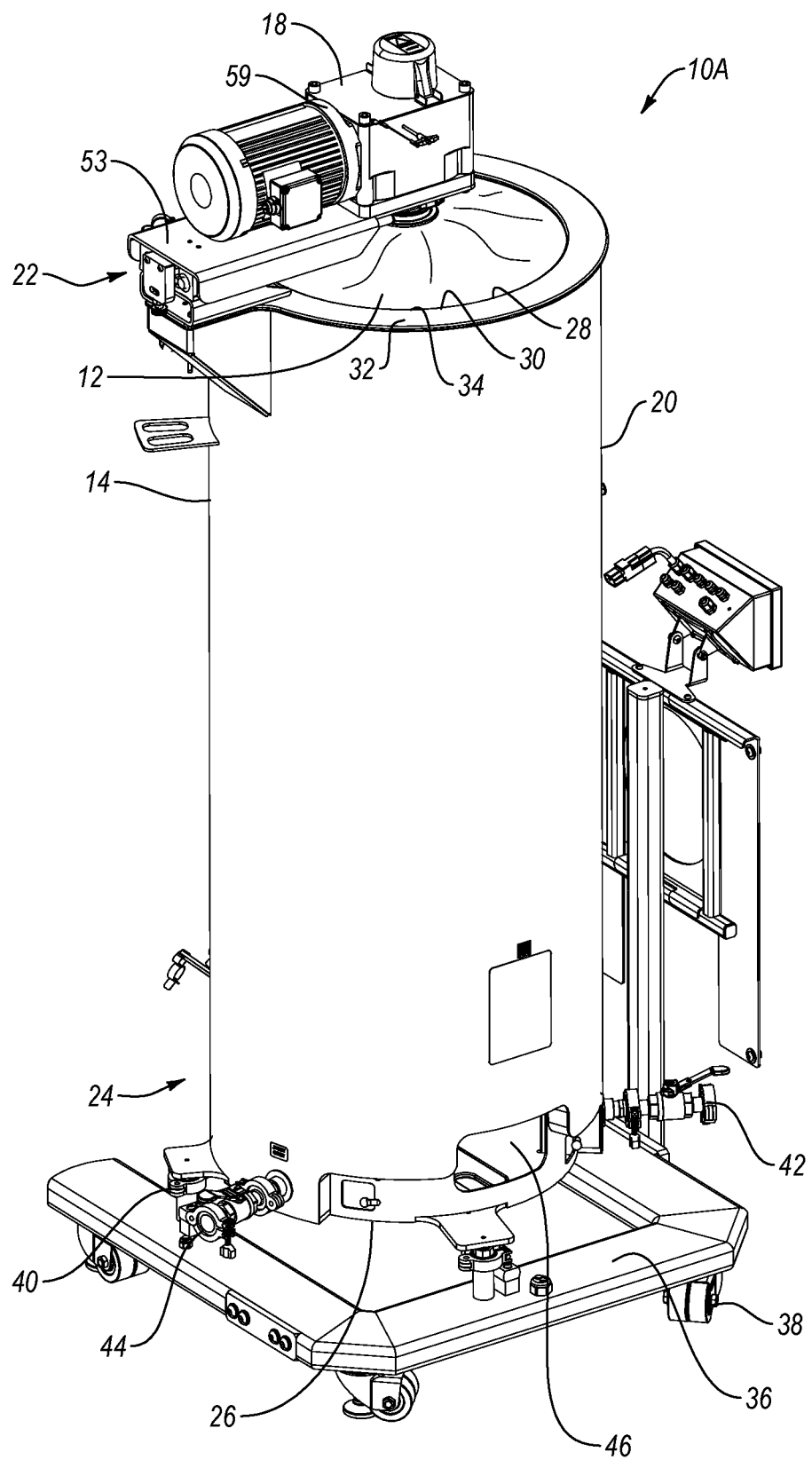
FIG. 1 is a perspective view of one embodiment of a fluid mixing system.

Before describing the present disclosure in detail, it is to be understood that this disclosure is not limited to particularly exemplified apparatus, systems, methods, or process parameters that may, of course, vary. It is also to be understood that the terminology used herein is only for the purpose of describing particular embodiments of the present disclosure, and is not intended to limit the scope of the disclosure.

All publications, patents, and patent applications cited herein, whether supra or infra, are hereby incorporated by reference in their entirety to the same extent as if each individual publication, patent, or patent application was specifically and individually indicated to be incorporated by reference.

The term "comprising" which is synonymous with "including," "containing," "having" or "characterized by," is inclusive or open-ended and does not exclude additional, unrecited elements or method steps.

It will be noted that, as used in this specification and the appended claims, the singular forms "a," "an" and "the" include plural referents unless the content clearly dictates otherwise. Thus, for example, reference to a "port" includes one, two, or more ports.

As used in the specification and appended claims, directional terms, such as "top," "bottom," "left," "right," "up," "down," "upper," "lower," "inner," "outer," "internal," "external," "interior," "exterior," "proximal," "distal" and the like are used herein solely to indicate relative directions and are not otherwise intended to limit the scope of the disclosure or claims.

Where possible, like numbering of elements have been used in various figures. Furthermore, alternative configurations of a particular element may each include separate letters appended to the element number. Accordingly, an appended letter can be used to designate an alternative design, structure, function, implementation, and/or embodiment of an element or feature without an appended letter. For instance, an element "80" may be embodied in an alternative configuration and designated "80a." Similarly, multiple instances of an element and or sub-elements of a parent element may each include separate letters appended to the element number. In each case, the element label may be used without an appended letter to generally refer to instances of the element or any one of the alternative elements. Element labels including an appended letter can be used to refer to a specific instance of the element or to distinguish or draw attention to multiple uses of the element.

Various aspects of the present devices, systems, and methods may be illustrated with reference to one or more exemplary embodiments. As used herein, the term "embodiment" means "serving as an example, instance, or illustration," and should not necessarily be construed as preferred or advantageous over other embodiments disclosed herein.

Various aspects of the present devices and systems may be illustrated by describing components that are coupled, attached, and/or joined together. As used herein, the terms "coupled", "attached", "connected" and/or "joined" are used to indicate either a direct connection between two components or, where appropriate, an indirect connection to one another through intervening or intermediate components. In contrast, when a component is referred to as being "directly coupled", "directly attached", "directly connected" and/or "directly joined" to another component, there are no intervening elements present.

Unless defined otherwise, all technical and scientific terms used herein have the same meaning as commonly understood by one of ordinary skill in the art to which the present disclosure pertains. Although a number of methods and materials similar or equivalent to those described herein can be used in the practice of the present disclosure, the preferred materials and methods are described herein.

The present disclosure relates to fluid mixing systems having modular impellers and related methods for mixing solutions and/or suspensions. In one embodiment, the mixing systems can be bioreactors or fermentors used for culturing cells or microorganisms. By way of example and not by limitation, the disclosed systems can be used in culturing bacteria, fungi, algae, plant cells, animal cells, protozoans, nematodes, and the like. The systems can accommodate cells and microorganisms that are aerobic or anaerobic and are adherent or non-adherent. The systems can also be used in association with the formation and/or treatment of solutions and/or suspensions that are not biological but nevertheless incorporate mixing. For example, the systems can be used in the production of media, chemicals, food products, beverages, and other liquid products.

The disclosed systems are designed so that a majority of the system components that contact the material being processed can be disposed of after each use. As a result, the inventive systems substantially eliminate the burden of cleaning and sterilization required by conventional stainless steel mixing and processing systems. This feature also ensures that sterility can be consistently maintained during repeated processing of multiple batches. In view of the foregoing, and the fact that the inventive systems are easily scalable, relatively low cost, and easily operated, the inventive systems can be used in a variety of industrial and research facilities that previously outsourced such processing.

Depicted in FIG. 1 is one embodiment of an inventive fluid mixing system 10A incorporating features of the present disclosure. In general, mixing system 10A comprises a container 12 that is disposed within a rigid support housing 14. A mixer assembly 18 is designed for mixing and/or suspending components within container 12. The various components of fluid mixing system 10A will now be discussed in greater detail.

With continued reference to FIG. 1, support housing 14 has a substantially cylindrical sidewall 20 that extends between an upper end 22 and an opposing lower end 24. Lower end 24 has a floor 26 mounted thereto. Support housing 14 has an interior surface 28 that bounds a chamber 30. An annular lip 32 is formed at upper end 22 and bounds an opening 34 to chamber 30. Floor 26 of support housing 14 rests on a cart 36 having wheels 38. Support housing 14 is removable secured to cart 36 by connectors 40. Cart 36 enables selective movement and positioning of support housing 14. In alternative embodiments, however, support housing 14 need not rest on cart 36 but can rest directly on a floor or other structure.

Although support housing 14 is shown as having a substantially cylindrical configuration, in alternative embodiments support housing 14 can have any desired shape capable of at least partially bounding a compartment. For example, sidewall 20 need not be cylindrical but can have a variety of other transverse, cross sectional configurations such as polygonal, elliptical, or irregular. Furthermore, it is appreciated that support housing 14 can be scaled to any desired size. For example, it is envisioned that support housing 14 can be sized so that chamber 30 can hold a volume of less than 50 liters or more than 1,000 liters. Support housing 14 is typically made of metal, such as stainless steel, but can also be made of other materials capable of withstanding the applied loads of the present disclosure.

In one embodiment of the present disclosure means are provided for regulating the temperature of the fluid that is contained within container 12 disposed within support housing 14. By way of example and not by limitation, electrical heating elements can be mounted on or within support housing 14. The heat from the heating elements is transferred either directly or indirectly to container 12. Alternatively, in the depicted embodiment support housing 14 is jacketed with one or more fluid channels being formed therein. The fluid channels have a fluid inlet 42 and a fluid outlet 44 that enables a fluid, such as water or propylene glycol, to be pumped through the fluid channels. By heating, cooling or otherwise controlling the temperature of the fluid that is passed through the fluid channels, the temperature of support housing 14 can be regulated which in turn regulates the temperature of the fluid within container 12 when container 12 is disposed within support housing 14. Other conventional means can also be used. When using container 12 as part of a bioreactor or fermentor, the means for heating can be used to heat the culture within container 12 to a temperature in a range between about 30° C. to about 40° C. Other temperatures can also be used.

Support housing 14 can have one or more opening 46 formed on the lower end of sidewall 20 and on floor 26 to enable gas and fluid lines to couple with container 12 and to enable various probes and sensors to couple with container 12 when container 12 is within support housing 14. Further disclosure on support housing 14 and alternative designs thereof is disclosed in U.S. Pat. No. 7,682,067 and US Patent Publication No. 2011-0310696, which are incorporated herein by specific reference.

Figure 2:
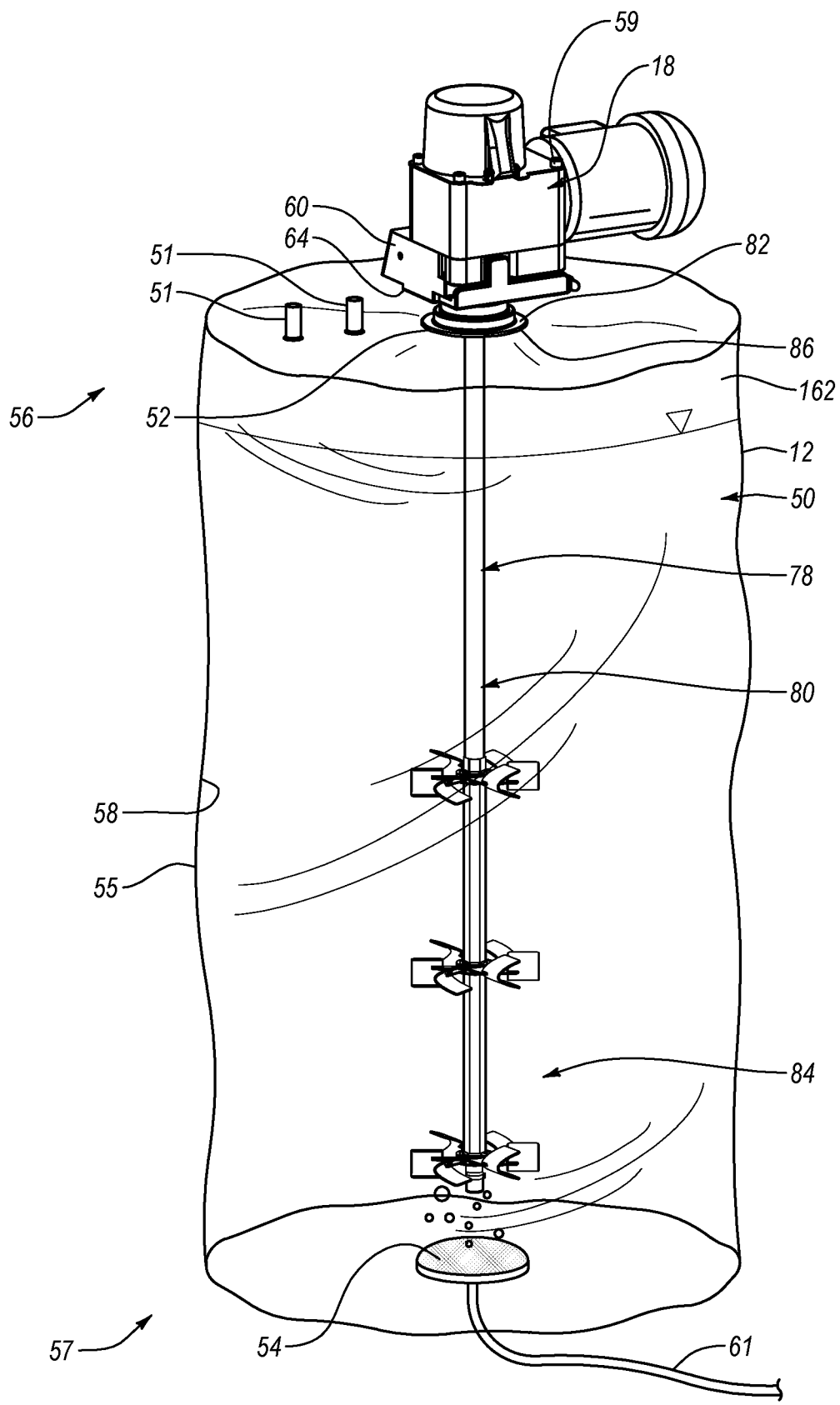
FIG. 2 is a perspective view of the container assembly and drive motor assembly of the fluid mixing system shown in FIG. 1.

FIG. 2 shows container 12 coupled with mixer assembly 18. Container 12 has a side 55 that extends from an upper end 56 to an opposing lower end 57. Container 12 also has an interior surface 58 that bounds a compartment 50 in which a portion of mixer assembly 18 is disposed. In the embodiment depicted, container 12 comprises a flexible bag. Formed on container 12 are a plurality of ports 51 that communicate with compartment 50. Although only two ports 51 are shown, it is appreciated that container 12 can be formed with any desired number of ports 51 and that ports 51 can be formed at any desired location on container 12 such as upper end 56, lower end 57, and/or alongside 55. Ports 51 can be the same configuration or different configurations and can be used for a variety of different purposes. For example, ports 51 can be coupled with fluid lines for delivering media, cell cultures, and/or other components into and out of container 12.

Ports 51 can also be used for coupling probes to container 12. For example, when container 12 is used as a bioreactor for growing cells or microorganisms, ports 51 can be used for coupling probes such as temperatures probes, pH probes, dissolved oxygen probes, and the like. Examples of ports 51 and how various probes and lines can be coupled thereto is disclosed in United States Patent Publication No. 2006-0270036, published Nov. 30, 2006 and United States Patent Publication No. 2006-0240546, published Oct. 26, 2006, which are incorporated herein by specific reference. Ports 51 can also be used for coupling container 12 to secondary containers and to other desired fittings.

In one embodiment of the present disclosure, means are provided for delivering a gas into the lower end of container 12. By way of example and not by limitation, as also depicted in FIG. 2, a sparger 54 can be either positioned on or mounted to lower end 57 of container 12 for delivering a gas to the fluid within container 12. As is understood by those skilled in the art, various gases are typically required in the growth of cells or microorganisms within container 12. The gas typically comprises air that is selectively combined with oxygen, carbon dioxide and/or nitrogen. However, other gases can also be used. The addition of these gases can be used to regulate the dissolved oxygen and $CO_2$ content and to regulate the pH of a culture solution. Depending on the application, sparging with gas can also have other applications. A gas line 61 is coupled with sparger 54 for delivering the desired gas to sparger 54. Gas line 61 need not pass through lower end 57 of container 12 but can extend down from upper end 56 or from other locations.

In the depicted embodiment, container 12 has an opening 52 that is sealed to a rotational or bearing assembly 82 of mixer assembly 18, which will be discussed below in greater detail. As a result, compartment 50 is sealed closed so that it can be sterilized and be used in processing sterile fluids. During use, container 12 is disposed within chamber 30 of support housing 14 as depicted in FIG. 1. Container 12 is supported by support housing 14 during use and can subsequently be disposed of following use. In one embodiment, container 12 comprised of a flexible, water impermeable material such as a low-density polyethylene or other polymeric sheets or film having a thickness in a range between about 0.1 mm to about 5 mm with about 0.2 mm to about 2 mm being more common. Other thicknesses can also be used. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive.

The extruded material comprises a single integral sheet that comprises two or more layers of different materials that can be separated by a contact layer. All of the layers are simultaneously co-extruded. One example of an extruded material that can be used in the present disclosure is the Thermo Scientific CX3-9 film available from Thermo Fisher Scientific. The Thermo Scientific CX3-9 film is a three-layer, 9 mil cast film produced in a cGMP facility. The outer layer is a polyester elastomer coextruded with an ultra-low density polyethylene product contact layer. Another example of an extruded material that can be used in the present disclosure is the Thermo Scientific CX5-14 cast film also available from Thermo Fisher Scientific. The Thermo Scientific CX5-14 cast film comprises a polyester elastomer outer layer, an ultra-low density polyethylene contact layer, and an EVOH barrier layer disposed therebetween.

The material is approved for direct contact with living cells and is capable of maintaining a solution sterile. In such an embodiment, the material can also be sterilizable such as by radiation. Examples of materials that can be used in different situations are disclosed in U.S. Pat. No. 6,083,587 which issued on Jul. 4, 2000 and United States Patent Publication No. US 2003-0077466 A1, published Apr. 24, 2003, which are hereby incorporated by specific reference.

In one embodiment, container 12 comprise a two-dimensional pillow style bag or a three-dimensional bag. Further disclosure with regard to one method of manufacturing three-dimensional bags is disclosed in United States Patent Publication No. US 2002-0131654 A1, published Sep. 19, 2002, which is hereby incorporated by reference.

It is appreciated that container 12 can be manufactured to have virtually any desired size, shape, and configuration. For example, container 12 can be formed having a compartment sized to 10 liters, 30 liters, 100 liters, 250 liters, 500 liters, 750 liters, 1,000 liters, 1,500 liters, 3,000 liters, 5,000 liters, 10,000 liters or other desired volumes. The size of the compartment can also be in the range between any two of the above volumes. Although container 12 can be any shape, in one embodiment container 12 is specifically configured to be complementary or substantially complementary to chamber 30 of support housing 14. It is desirable that when container 12 is received within chamber 30, container 12 is at least generally uniformly supported by support housing 14. Having at least general uniform support of container 12 by support housing 14 helps to preclude failure of container 12 by hydraulic forces applied to container 12 when filled with fluid.

Although in the above discussed embodiment container 12 can comprise a flexible, collapsible bag, in alternative embodiments it is appreciated that container 12 can comprise any form of collapsible container or semi-rigid container. Container 12 can also be transparent or opaque and can have ultraviolet light inhibitors incorporated therein.

Mixer assembly 18 is used for mixing and/or suspending a culture or other solution or suspension within container 12. As depicted in FIGS. 2, mixer assembly 18 generally comprises a drive motor assembly 59 that is mounted on support housing 14 (FIG. 1), an impeller assembly 78 coupled to and projecting into container 12, and a drive shaft 72 (FIG. 4) that extends between drive motor assembly 59 and impeller assembly 78.

Figure 3:
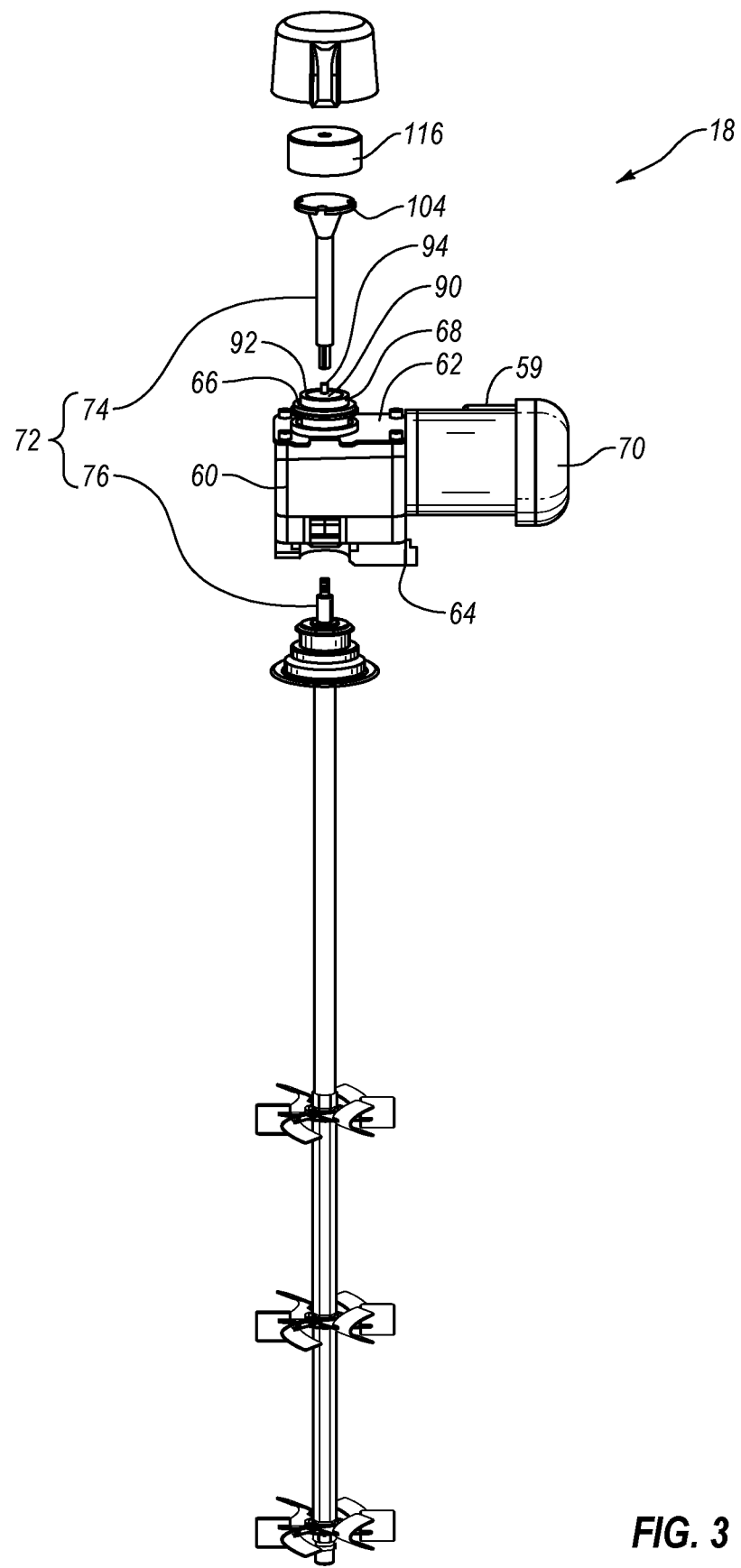
FIG. 3 is a partially exploded elevational side view of the impeller assembly, drive shaft and drive motor shown in FIG. 2.
Figure 4:
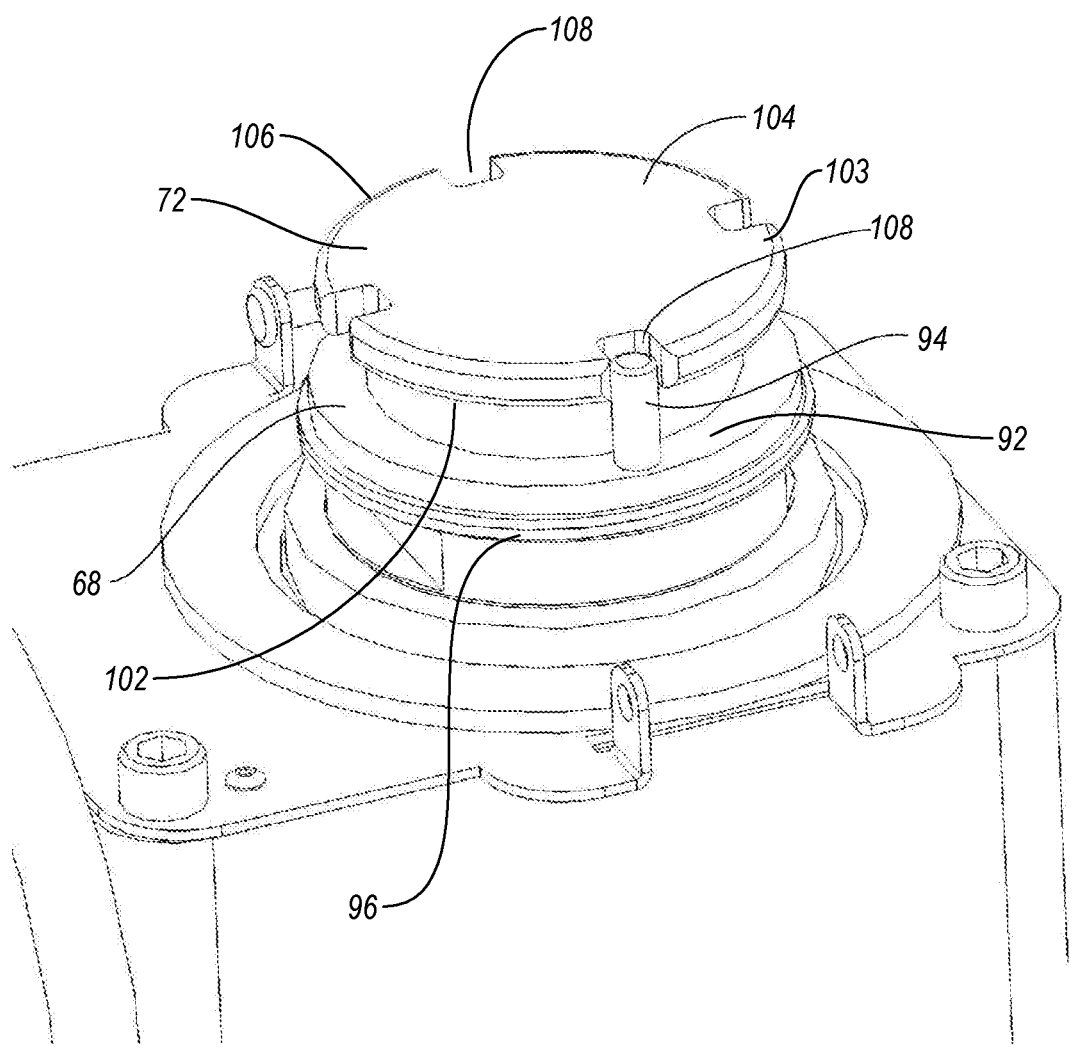
FIG. 4 is a perspective view of the drive shaft in FIG. 3 being coupled with the drive motor assembly.

Turning to FIG. 3, drive motor assembly 59 comprises a housing 60 having a top surface 62 and an opposing bottom surface 64 with an opening 66 extending through housing 60 between surfaces 62 and 64. A tubular motor mount 68 is rotatably secured within opening 66 of housing 60 and bounds a passage 90 extending therethrough. As depicted in FIG. 4, the upper end of motor mount 68 terminates at an end face 92 having a locking pin 94 outwardly projecting therefrom. A thread 96 encircles motor mount 68 adjacent to end face 92. Returning to FIG. 3, a drive motor 70 is mounted to housing 60 and engages with motor mount 68 so as to facilitate select rotation of motor mount 68 relative to housing 60. As depicted in FIG. 1, drive motor assembly 59 is coupled with support housing 14 by a bracket 53. In alternative embodiments, however, drive motor assembly 59 can be mounted on a separate structure adjacent to support housing 14.

Figure 5:
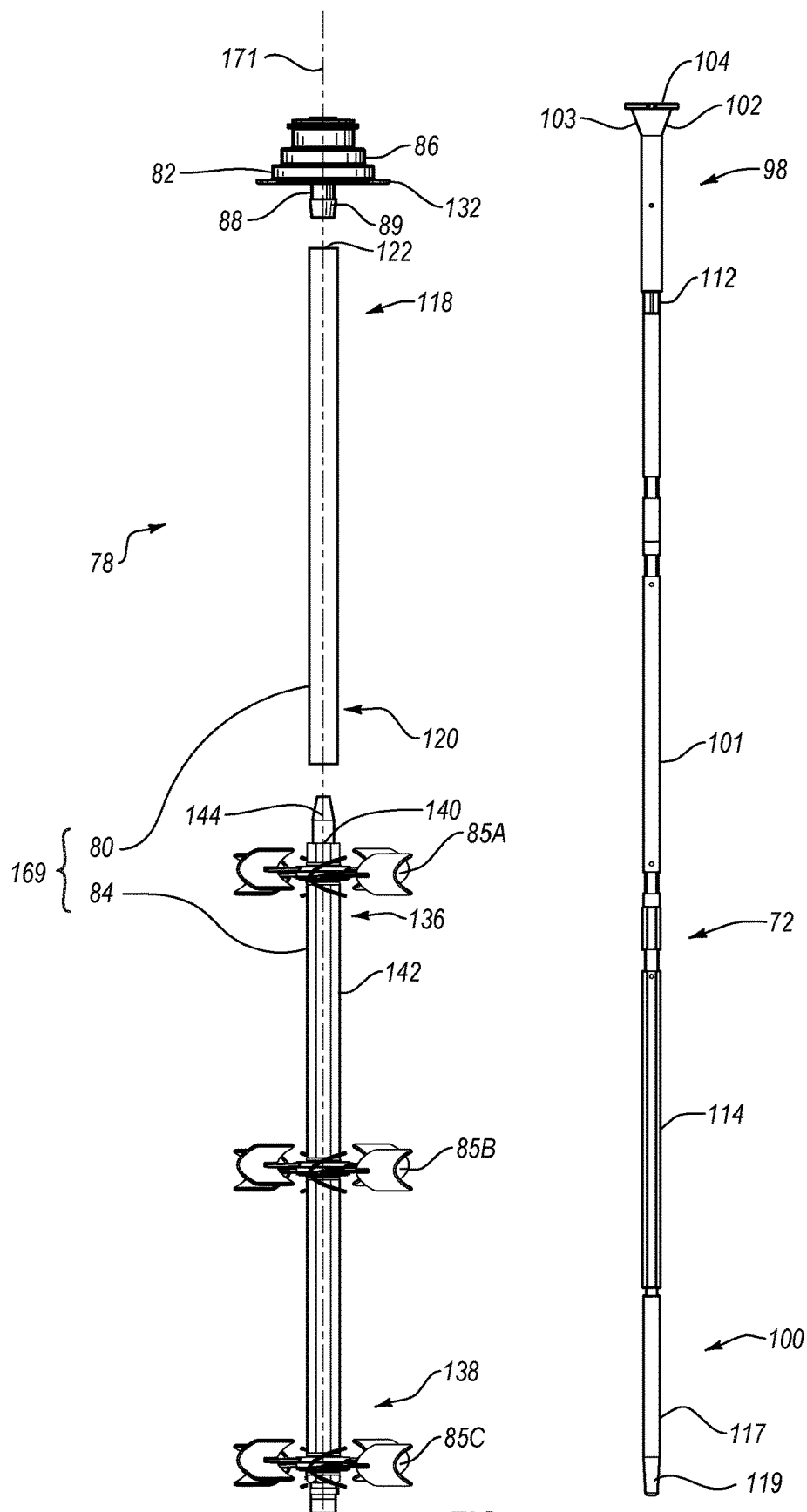
FIG. 5 is an exploded elevated side view of the impeller assembly and drive shaft shown in FIG. 3.

Drive shaft 72 is configured to pass through motor mount 68 and thus through housing 60. Turning to FIG. 5, drive shaft 72 has a first end 98 and an opposing second end 100 and generally comprises a shaft portion 101 with a head 103 mounted on the end thereof. Head 103 includes a substantially frustoconical engaging portion 102 that is complimentary to an engaging portion formed within the upper end of motor mount 68. As a result, the two engaging portions can be complementary mated to facilitate contacting engagement between motor mount 68 and drive shaft 72 when drive shaft 72 is passed through motor mount 68.

As depicted in FIG. 4, head 103 also includes a substantially circular plate 104 disposed on top of engaging portion 102. Plate 104 extends to a perimeter edge 106 that radially outwardly projects beyond engaging portion 102. A plurality of spaced apart notches 108 are formed on perimeter edge 106. When drive shaft 72 is passed through motor mount 68, plate 104 rests on or slightly above end face 92 of motor mount 68 so that locking pin 94 is received within a notch 108. As a result, drive shaft 72 is locked to motor mount 68 so that rotation of motor mount 68 facilitates concurrent rotation of drive shaft 72. A cap 116 (FIG. 3) can be threaded onto the end of motor mount 68 to prevent drive shaft 72 from disengaging from motor mount 68.

Returning to FIG. 5, shaft portion 101 comprises a first driver portion 112 and a second driver portion 114. Driver portions 112 and 114, as will be discussed below in greater detail, typically have a polygonal transverse cross section. For example, driver portions 112 and 114 can have 5, 6, 7, or more sides. In other embodiments, the transverse cross of section of driver portions 112 and 114 can be other non-circular shapes such as oval or irregular. The remainder of shaft portion 101 typically has a circular transverse cross section with a maximum diameter that is smaller than the maximum diameter of driver portions 112 and 114. A second end 117 of drive shaft 72 terminates at a nose 119 that is inwardly tapered for easy insertion.

In one embodiment drive shaft 72 can comprise a single, unitary shaft. In other embodiments, draft shaft 72 can be comprised of multiple sections that are selectively threaded or otherwise secured together. For example, drive shaft 72 can comprise a head section 74 and a separate shaft section 76 that can be coupled together as depicted in FIG. 3. Drive shaft 72 can be formed from 2, 3, 4, 5 or more sections that are selectively coupled together. Drive shaft 72 can be comprised of high strength polymers, ceramics, composites, metals, such as aluminum, stainless steel, or other metal alloys, or other materials. Furthermore, different sections can be made of different materials.

By forming drive shaft 72 from multiple sections, it is easy to form a shaft having a desired length by adding or removing sections. Furthermore, the modular drive shaft 72 can be used in a room with a low ceiling height. For example, a first section of drive shaft 72 can be partially advanced down through motor mount 68. Additional sections can then be progressively attached thereto as the sections are progressively advanced down through motor mount 68. Accordingly, the full length of drive shaft 72 need not be simultaneously raised above motor mount 68 for passing therethrough. Alternative embodiments of drive shafts that can be used in the present inventive system, including examples of how separate sections can be coupled together, are disclosed in U.S. Pat. No. 8,641,314 which issued on Feb. 4, 2014 and which is incorporated herein by specific reference.

As depicted in FIG. 5, impeller assembly 78 comprises an elongated first tubular connector 80 having bearing assembly 82 secured at one end and an elongated second tubular connector 84 coupled at the opposing end. A plurality of impellers 85A-C are disposed along the length of second tubular connector 84. More specifically, first tubular connector 80 has a first end 118 and an opposing second end 120 with an interior surface that bounds a passage 122 that extends along the length thereof. In one embodiment first tubular connector 80 comprises a flexible tube that can typically be bent along its length over and angle of 90° and more commonly 180° or 270° without plastic deformation and/or can be twisted about its longitudinal axis over and angle of 90° and more commonly 180° or 270° without plastic deformation. Tubular connector 80 is typically made from, comprises or consists of a sufficiently flexible material, such as an elastomeric material, so that tubular connector can withstand repeated bending and deformation without appreciable structural yield and can possess a durometer on the Shore OO scale that is typically less than 98 and often less than 60 or 30. Other values can also be used. First tubular connector 80 can be formed from a polymeric material such flexible PVC or other polymers having the desired properties.

Figure 6:
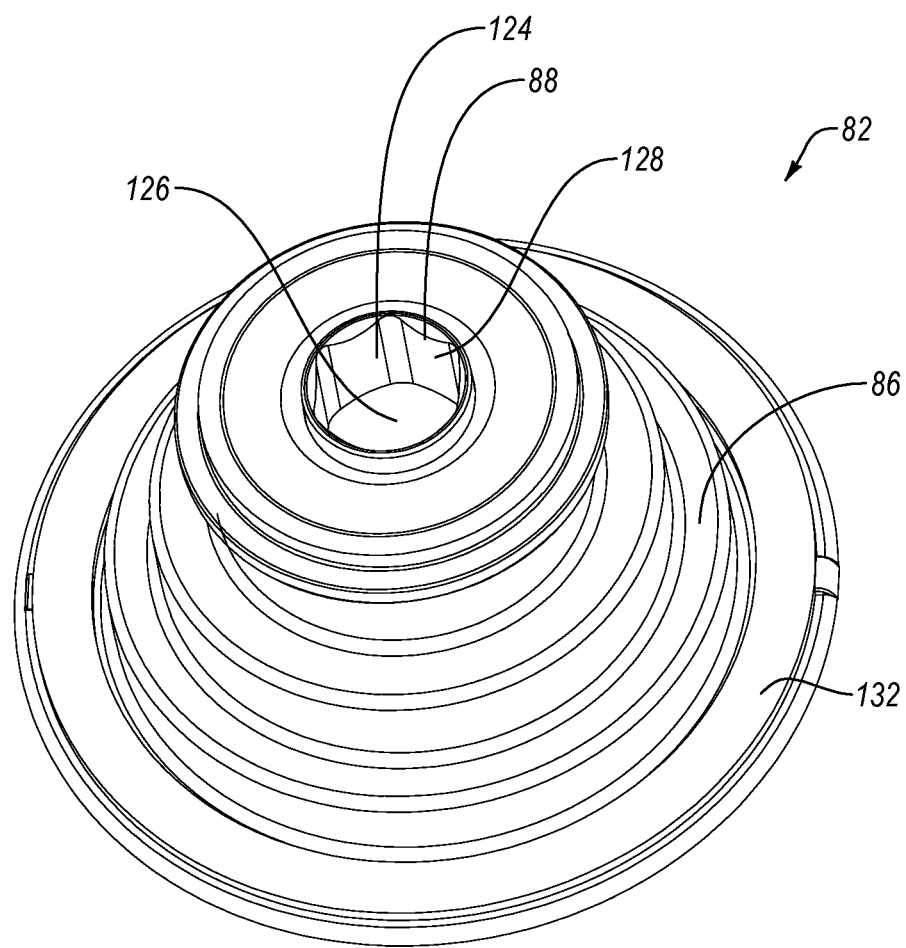
FIG. 6 is an enlarged top perspective view of the bearing assembly shown in FIG. 5.

Bearing assembly 82 comprises an outer casing 86 and a tubular hub 88 that centrally extends through outer casing 86 and is rotatably coupled thereto. One or more dynamic seals can be formed between outer casing 86 and tubular hub 88 so that a sterile seal can be maintained therebetween. Furthermore, one or more bearings can be positioned between outer casing 86 and tubular hub 88 to enable easy rotation of hub 88 relative to casing 86. As depicted in FIG. 6, hub 88 has an interior surface 124 that bound a passage 126 extending therethrough. At least a section of interior surface 124 forms an engaging portion 128 that is complementary to the transverse cross section of first driver portion 112 on drive shaft 72 (FIG. 5) or is otherwise configured to engage first driver portion 112 so that when first driver portion 112 is received within engaging portion 128, rotation of drive shaft 72 facilitates rotation of hub 88 relative to casing 86.

Returning to FIG. 5, hub 88 includes a barbed stem 89 that downwardly projects below casing 86. Stem 89 is configured to be received within first end 118 of first tubular connector 80 so that a liquid tight seal is formed therebetween and so that stem 89 is secured to first tubular connector 80. Casing 86 includes an annular, outwardly projecting flange 132 which, as depicted in FIG. 2, is welded or otherwise secured to container 12 so as to secure casing to container 12 within opening 52 thereof. In this configuration, first tubular connector 80 projects into compartment 50 of container 12.

Returning to FIG. 5, second tubular connector 84 has a first end 136 and an opposing second end 138 with an interior surface 140 and an exterior surface 142 extending therebetween. Interior surface 140 bounds a passage 141 (FIG. 23) extending therethrough. In one embodiment, second tubular connector 84 is more rigid than first tubular connector 80. For example, in different embodiments second tubular connector 84 cannot be bent along its length over and angle of 20°, 40°, 90° or 120° without plastic deformation and/or cannot be twisted about its longitudinal axis over and angle of 20°, 40°, 90° or 120° without plastic deformation. Tubular connector 84 is typically not made from and does not comprise or consists of an elastomeric material. Rather, tubular connector 84 is typically comprised of a rigid plastic or other material so that tubular connector 84 has a durometer on the Shore D scale that is typically greater than 20 and often greater than 40 or 60. Other values can also be used.

Figure 7:
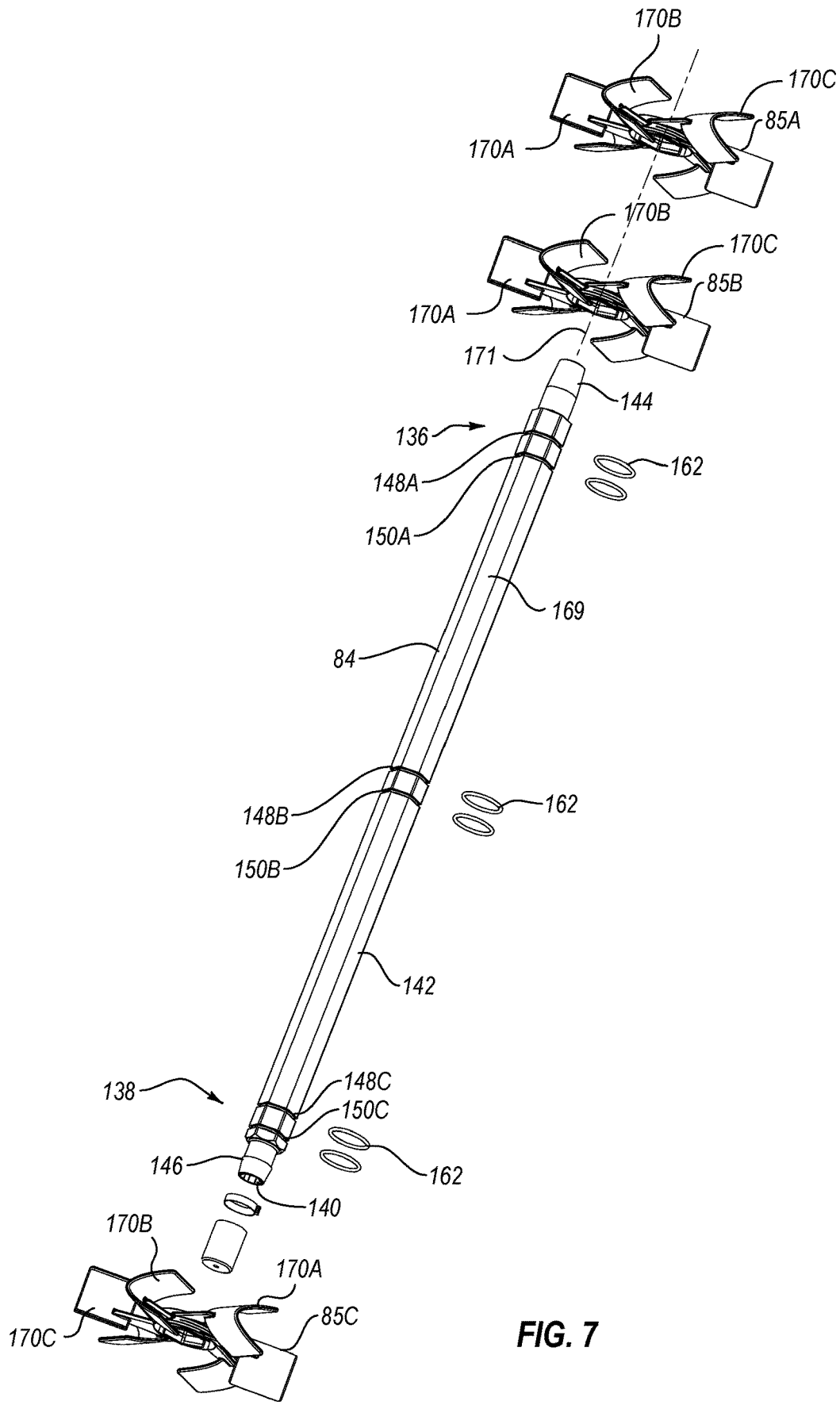
FIG. 7 is an exploded perspective view of the second tubular connector and impellers shown in FIG. 5.

As depicted in FIG. 7, formed at first end 136 is a tapered stem 144 that is configured to be received within second end 120 of first tubular connector 80 (FIG. 5) so as to form a secure, liquid tight seal therebetween. A barbed stem 146 is formed at second end 138. Exterior surface 142 extending between stems 144 and 146 has a transverse cross section that is polygonal, elliptical, or some other non-circular configuration. For example, the transverse cross section can be polygonal having 3, 4, 5, 6, 7, 8 or more sides. Disposed at spaced apart locations along the length of exterior surface 142 are three pairs of annular grooves 148A-C and 150A-C that encircle second tubular connector 84.

With reference to FIG. 5, first tubular connector 80 and second tubular connector 84 combine to form an elongated drive member 169. Each of first tubular connector 80, second tubular connect 84, and combined drive member 169 have a central longitudinal axis 171 extending along the length thereof. In this embodiment, axis 171 is also the rotational axis about which first tubular connector 80, second tubular connect 84, and combined drive member 169 rotate during operation. In one alternative embodiment, first tubular connector 80 can be made of the same material as second tubular connector 84. In another alternative embodiment, first tubular connector 80 can be eliminated and drive member 169 can comprise only an elongated second tubular connector 84 that is coupled directly to bearing assembly 82 and has a plurality of impellers 85 mounted thereon.

Figure 9:
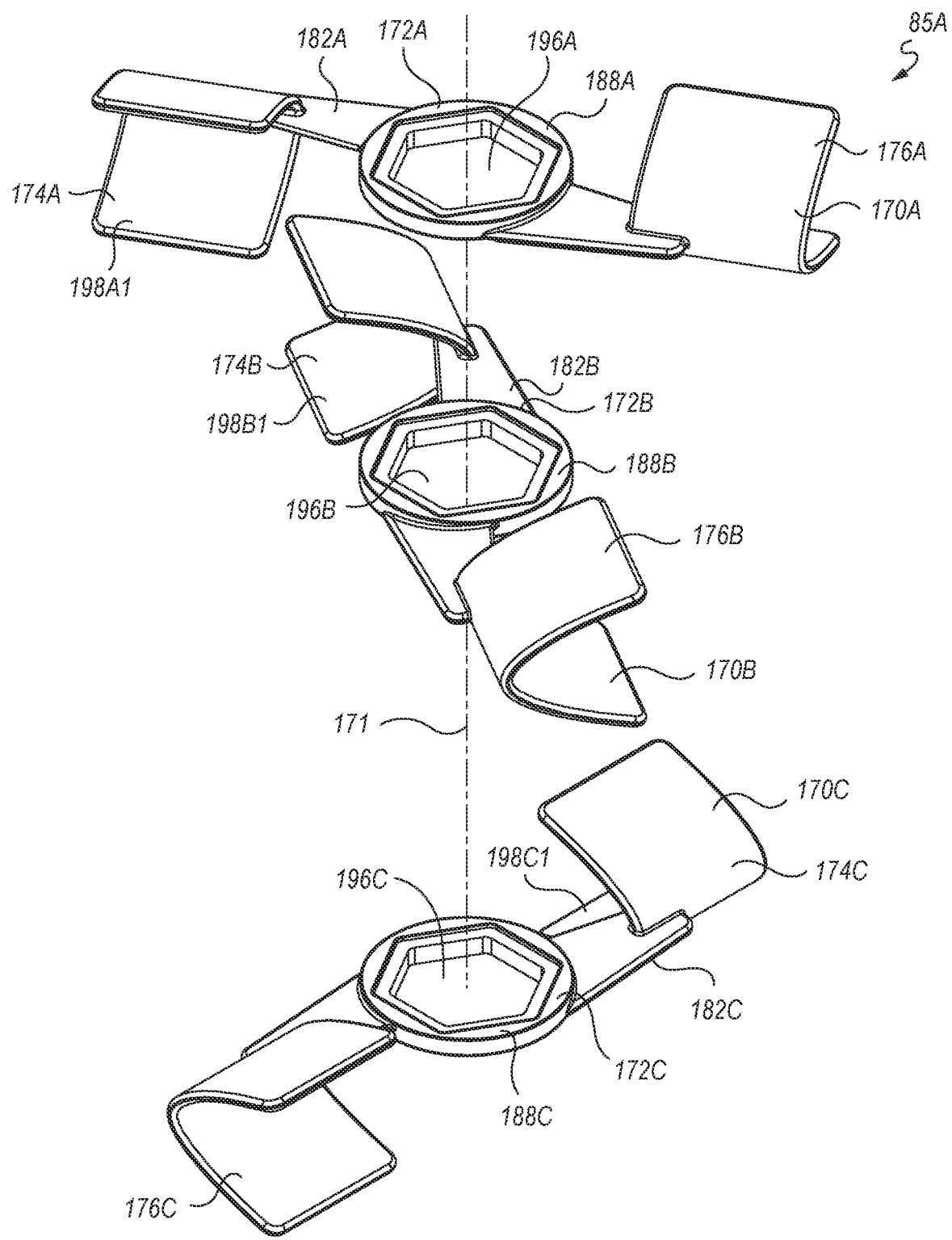
FIG. 9 is an exploded view of the impeller shown in FIG. 8.

Continuing with the embodiment in FIG. 5, exterior surface 142 of second tubular connector 84 is configured to receive impellers 85A-C so that they can be fixed thereon. In the current embodiment, each impeller 85A-C is modular and comprises a plurality of impeller segments that act together to form impellers 85A-C. Specifically, as depicted in FIG. 9, impeller 85A comprises a first impeller segment 170A, a second impeller segment 170B and a third impeller segment 170C. As better shown in FIG. 10, first impeller segment 170A comprises a first mount 172A having a first mixing blade 174A and a second mixing blade 176A mounted thereon. More specifically, first mount 172A has a top face 178A and an opposing bottom face 180A that extend to an outer perimeter edge 182A. In the current embodiment, first mount 172A is elongated so that top face 178A and opposing bottom face 180A extend to opposing terminal tips 184A and 186A. Expressed in other terms, first mount 172A can be defined has having a hub 188A with a perimeter edge 189A and a pair of arms 190A and 192A that outwardly projecting from opposing sides of perimeter edge 189A. Arm 190A terminates at terminal tip 184A while arm 192A terminates at tip 186A.

Figure 10:
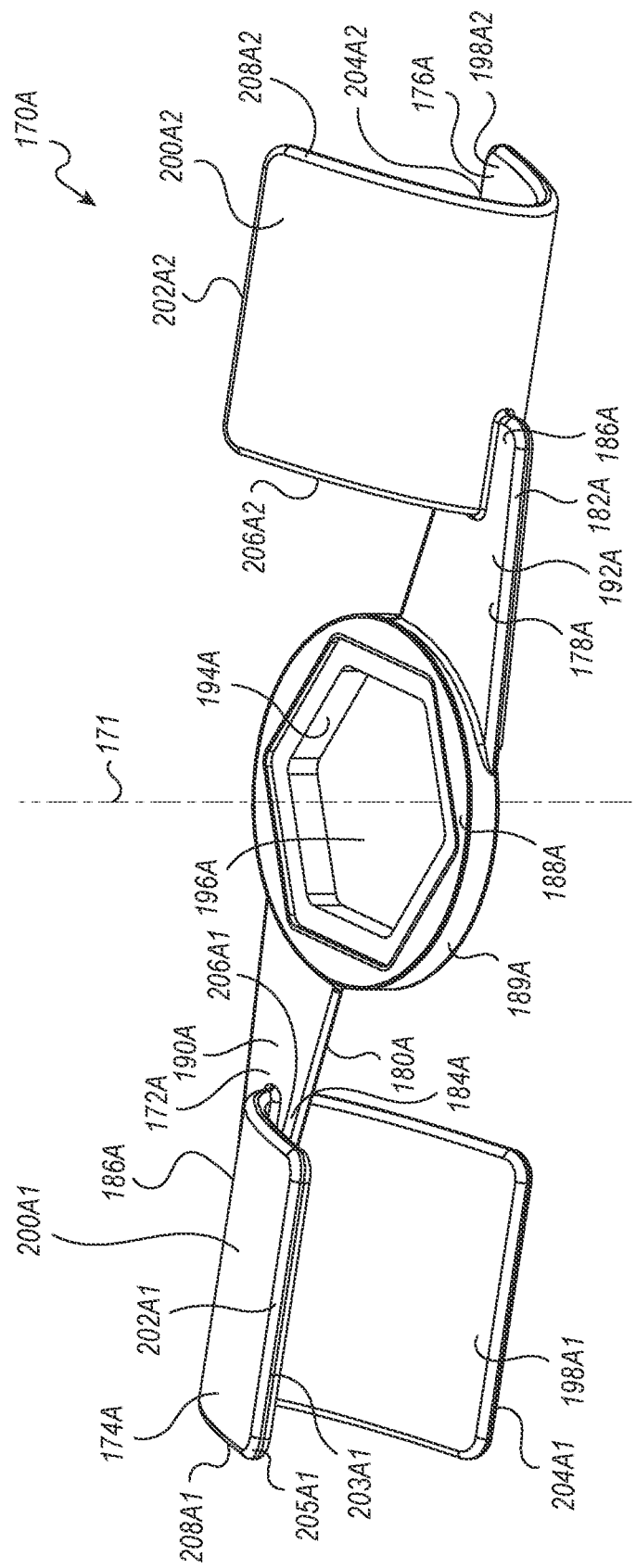
FIG. 10 is a perspective view of one of the impeller segments shown in FIG. 9.

With continued reference to FIGS. 5, 9, and 10, first mount 172A or hub 188A has an interior surface 194A that bounds an opening 196A that extends between opposing faces 178A and 180A. Interior surface 194A has a configuration complementary to exterior surface 142 of second tubular connector 84 (FIG. 7) or is otherwise configured to engage exterior surface 142 so that when second tubular connector 84 is advanced through opening 196A of impeller segment 170A, impeller segment 170A is keyed with or otherwise secured to second tubular connector 84. Accordingly, rotation of second tubular connector 84 about axis 171 causes impeller segment 170A to concurrently rotate therewith. As such, opening 196A can have a polygonal or other non-circular transverse cross section as previously discussed above with regard to second tubular connector 84. Opening 196A passes through hub 188A and, in the depicted embodiment, centrally passes through first mount 172A.

At least a portion of mixing blades 174A and 176A outwardly project from outer perimeter edge 182A of first mount 172A and are spaced apart. More specifically, first mixing blade 174A outwardly projects from terminal tip 184A while second mixing blade 176A outwardly projects from terminal tip 186A. First mixing blade 174A has a front face 198A1 and an opposing back face 200A1 each having a length that extends from a first terminal end 202A1 to an opposing second terminal end 204A1 and having a width that extends from an inside edge 206A1 to an opposing outside edge 208A1. Inside edge 206A1 is connected directly to first mount 172A while outside edge 206A1 is spaced apart from first mount 172A.

With continued reference to FIG. 10, front face 198A1 of first mixing blade 174A extends in a curve between the first terminal end 202A1 and the opposing second terminal end 204A1. In one embodiment, the curvature of front face 198A1 is a concave curvature or can more specifically be a parabolic curvature. In other embodiments, front face 198A1 can have a V-shape or C-shape configuration. Similarly, back face 200A1 of first mixing blade 174A extends in a curve between the first terminal end 202A1 and the opposing second terminal end 204A1. In one embodiment, the curvature of back face 200A1 is a convex curvature. The curvature of front face 198A1 and back face 200A1 can be complementary so that there is a constant thickness extending from terminal tips 202A1 and 204A1. As such, mixing blade 174A can have a parabolic configuration or in other embodiments have a V-shaped or C-shaped configuration. Alternatively, the thickness can vary along the length of first mixing blade 174A. In contrast to curving along the height, front face 198A1 and back face 200A1 can extend linearly along the width between edges 206A1 and 208A1. That is, along planes that extend normal axis 171, front face 198A1 and back face 200A1 are shown extending linearly between inside edge 206A1 and opposing outside edge 208A1.

Figure 11:
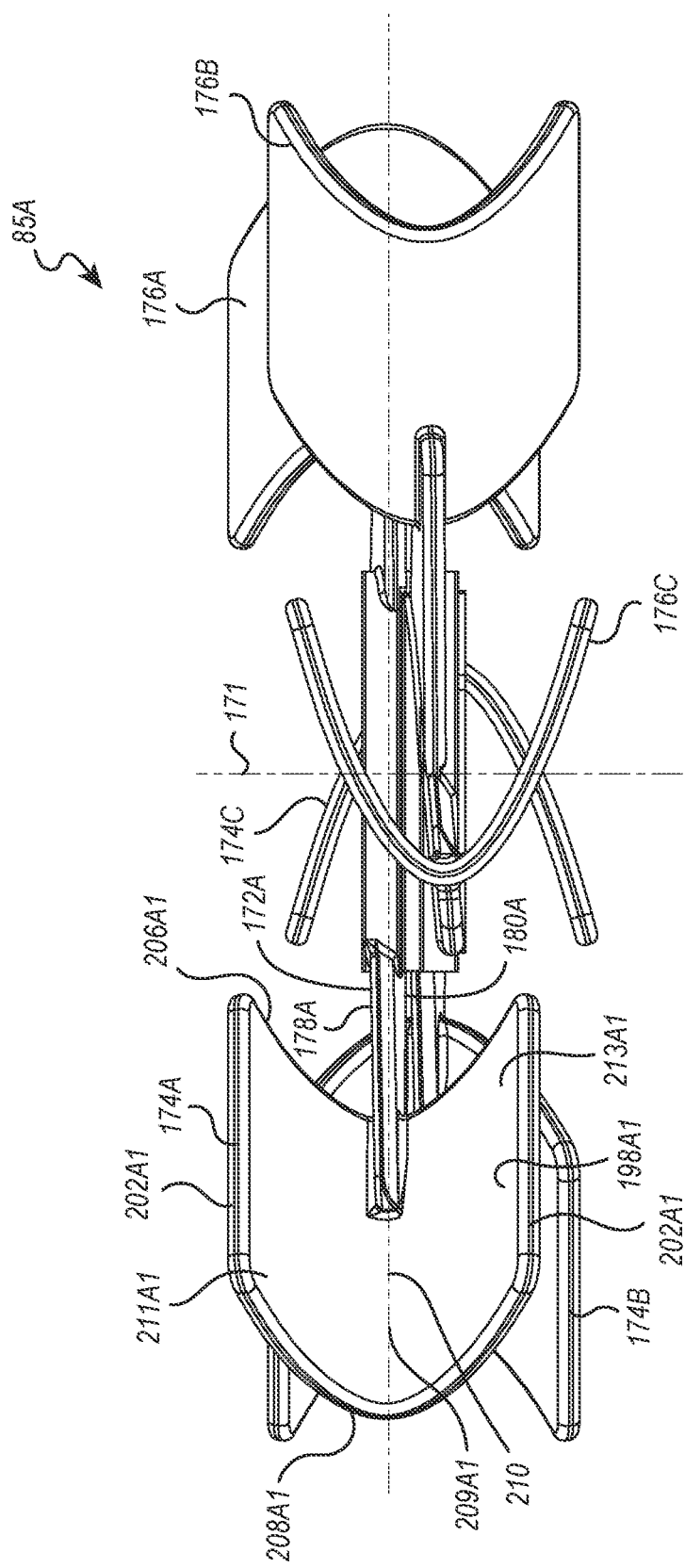
FIG. 11 is an elevated side view of the impeller shown in FIG. 8.

As depicted in FIG. 11, the curve of front face 198A1 of first mixing blade 174A has an apex 209A1 that extends along the width between inside edge 206A1 and opposing outside edge 208A1. In the depicted embodiment, first mixing blade 174A comprises a first wing 211A1 having a length extending from apex 209A1 to first terminal end 202A1 and a second wing 213A2 having a length extending from apex 209A1 to second terminal end 204A1. In this embodiment, the length of first wing 211A1 is equal to the length of second wing 213A2. Furthermore, first wing 211A1 and second wing 213A1 extend symmetrically on opposing sides of a plane 210 that passes through apex 209A1 and is disposed orthogonal to axis 171. It is also noted from FIG. 11 that first wing 211A1 projects outward from top face 178A of mount 172A while second wing 213A1 projects outward from bottom face 180A of mount 172A. As discussed below, in alternative embodiments, the length of first wing 211A1 can differ from the length of second wing 213A2. Furthermore, first wing 211A1 and second wing 213A2 can project asymmetrically about plane 210.

Returning to FIG. 10, in the current embodiment, second mixing blade 176A has the identical configuration, mounting and alternatives as first mixing blade 174A except that second mixing blade 176A is disposed at the opposing end of mount 172A, as discussed above. As such, all of the above discussion with regard to first mixing blade 174A and the mounting and alternatives thereof is also applicable to second mixing blade 176A. Like elements between mixing blades 174A and 176A are identified by like reference characters except that the reference characters for mixing blade 176A include the suffix "A2."

Returning to FIG. 9, each of impeller segments 170A, 170B, and 170C can have identical configurations. As such, all of the above discussion with regard to impeller segment 170A is also applicable to impeller segments 170B and 170C. Like elements between impeller segments 170A and 170B are identified by like reference characters except that the reference characters for impeller segment 170B include the suffix "B." Similarly, like elements between impeller segments 170A and 170C are identified by like reference characters except that the reference characters for impeller segment 170C include the suffix "C."

As discussed above, the combination of impeller segments 170A, 170B, and 170C form impeller 85A. In the current embodiment, each of impellers 85A, 85B and 85C have identical configurations. As such, with reference to FIG. 7, each of impellers 85B and 85C also include impeller segments 170A, 170B, and 170C as discussed above. Again, like elements are identified by like reference characters.

Figure 8:
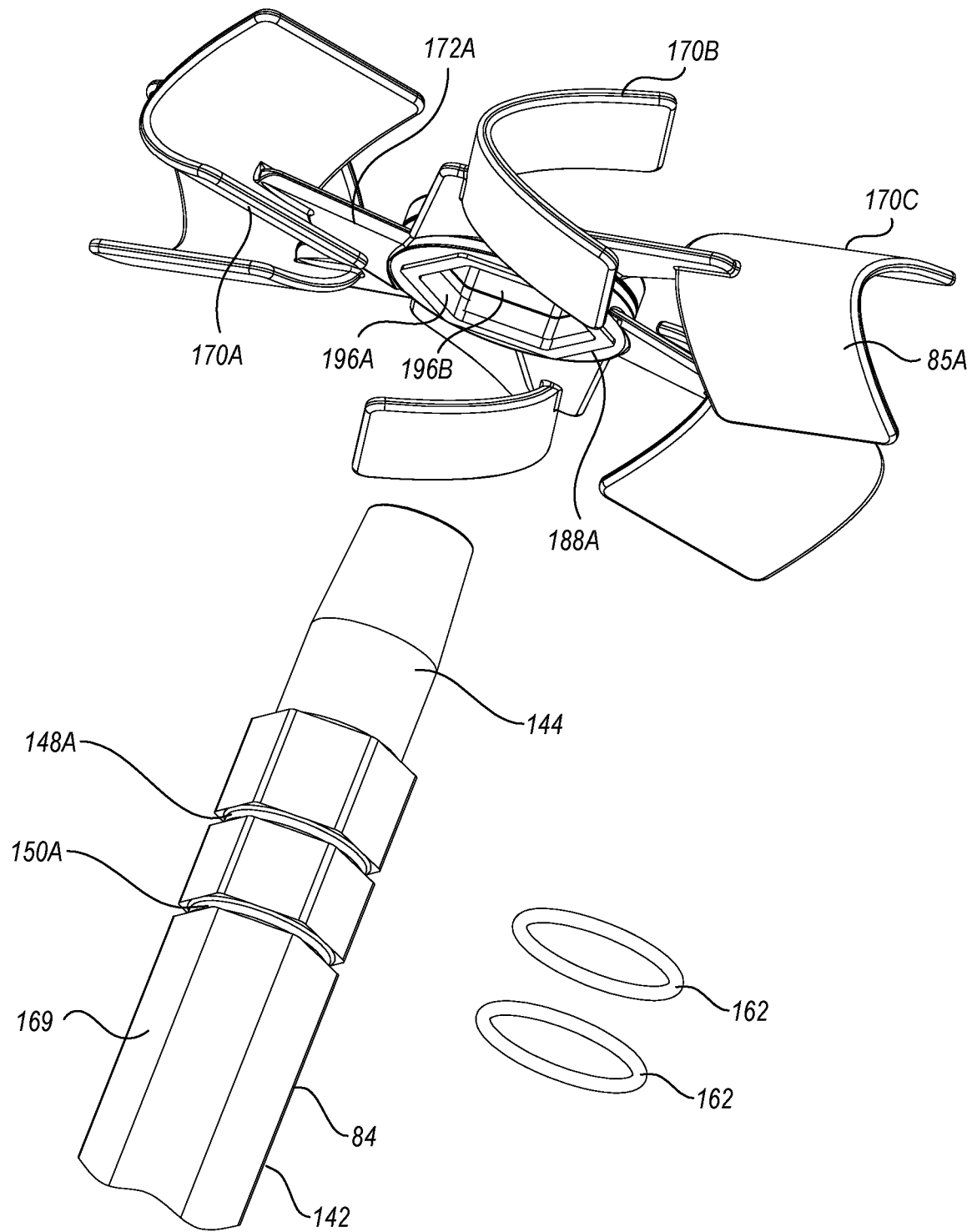
FIG. 8 is an enlarged, partially exploded perspective view of the first end of the second tubular connector and an impeller to be received thereon, based upon FIG. 5.

During assembly, each impeller segment 170A-170C is slid along second tubular connector 84/drive member 169 until mount 172/hub 188 is centrally located between a pair of corresponding grooves 148 and 150. For example, as shown in FIG. 8, an end of second tubular connector 84 can be advanced through opening 196A of impeller segment 170A until mount 172A/hub 188A is centrally located between a pair of corresponding grooves 148 and 150, e.g., grooves 148A and 150A. In this embodiment, each opening 196A-C of impeller segments 170A-C is in the form of a hexagon while exterior surface 142 of second tubular connector 84 has a corresponding hexagonal configuration. As such, once second tubular connector 84/drive member 169 is received within opening 196A, impeller segment 170A is precluded from rotating relative to second tubular connector 84/drive member 169.

Next, an end of second tubular connector 84/drive member 169 can be advanced through opening 196B of impeller segment 170B. In this case, however, impeller segment 170B is first rotated 60° relative to impeller segment 170A prior to receiving second tubular connector 84 so that impeller segments 170A and 170B are rotationally offset as shown in FIG. 8. Finally, impeller segment 170C is rotated 60° relative to impeller segment 170B so that each of impeller segments 170A-C are rotationally offset and an end of second tubular connector 84 can then be advanced through opening 196C (FIG. 9) of impeller segment 170C. Again, once second tubular connector 84 is advanced through openings 196B and 196C, impeller segments 170B and 170C are precluded from rotating relative to second tubular connector 84/drive member 169.

Each of impeller segments 170A-170C is slid along second tubular connector 84/drive member 169 until mount 172/hub 188 is centrally located between a pair of corresponding grooves 148 and 150. For example, with reference to FIG. 7, impeller segments 170A-C of impeller 85A can be positioned between grooves 148A and 150A, impeller segments 170A-C of impeller 85B can be positioned between grooves 148B and 150B, and impeller segments 170A-C of impeller 85C can be positioned between grooves 148C and 150C. Typically, impeller segments 170A-170C are butted against each other or are disposed directly adjacent to each other between grooves 148 and 150 and combine to function as a single impeller. If desired, small spacers can be positioned between impeller segments 170A-C as they are slid onto second tubular connector 84. It is also appreciated that impeller segments 170A-C can be slid on second tubular connector 84 consecutively or concurrently as a combined group.

Because each of impeller segments 170A-170C has two mixing blades 174 and 176, the resulting impellers 85A-C each have a total of six blades that are each uniformly, radially spaced apart. Although each pair of blades are slightly spaced apart along the length of second tubular connector 84/drive member 169, impeller segments 170A-170C are typically disposed so that a single plane 210 extending normal to the axis 171, i.e., the central longitudinal axis or the axis of rotation, of second tubular connector 84/drive member 169 can intersect with all six of mixing blades 174A-C and 176A-C as shown in FIG. 11. This assembly helps to ensure that the mixing blade are sufficiently close together that they interact to function as a single impeller. In other embodiment, that mixing blades can be spaced apart so that a single plane extending normal to axis 171 cannot intersect with each of the mixing blades. This embodiment, however, may have a decreased mixing efficiency.

Returning to FIG. 7, retainers 162 are received within each of grooves 148 and 150 to retain the assembled impeller segments 170A-170C, i.e., impellers 85A-C, at the desired locations along second tubular connector 84/drive member 169. In one embodiment, retainers 162 comprise O-rings that are made from an elastomeric material such as silicone. Other materials can also be used. The O-rings are configured so that when they are received within annular grooves 148/150, the O-rings still radially outwardly project beyond exterior surface 142 of second tubular connector 84. Thus, the O-rings/retainer 162 can be expanded to slid onto second tubular connector 84 on opposing sides of each impeller 85. O-rings/retainers 162 resiliently constrict when they are received within annular grooves 148/150 on the opposing sides of impellers 85A-C. However, the O-rings/ retainers 162 within annular grooves 148/150 radially, outwardly project beyond exterior surface 142 of second tubular connector 84 so as to preclude impellers 85A-C from sliding along the length of second tubular connector 84, i.e., sliding past the O-rings/retainer 162. See, for example, FIG. 12 showing O-ring/retainers 162 in annular groove 150C securing the placement of impeller 85C.

The above configuration provides a simple way to manufacture and assemble second tubular connector 84/drive member 169 with impellers 85 thereon and eliminates complex molding procedures and mechanical fasteners, such as set screws, which can become loose or can form small holes or crevices into which cells or microorganisms can stagnate and die. The configuration also eliminates the required use of adhesives which can potentially leach into and contaminate a culture.

In alternative embodiments, however, it is appreciated that other retainers 162 can also be used. For example, snap rings or clips, such as those having a C-shaped configuration, could be received within grooves 148/150 to secure impellers 85. In still other embodiments, it is appreciated that other conventional techniques could be used to secure impellers 85 in place on second tubular connector 84, such as welding, adhesive, clamps etc. Furthermore, in other alternative embodiments it is appreciated that not all of exterior surface 142 of second tubular connector 84 needs to be complementary to interior surface 158 of impellers 85. Rather, only the portion of exterior surface 142 between grooves 148 and 150 needs to have the complementary configuration or otherwise be configured to engage or mate with impellers 85.

Figure 12:
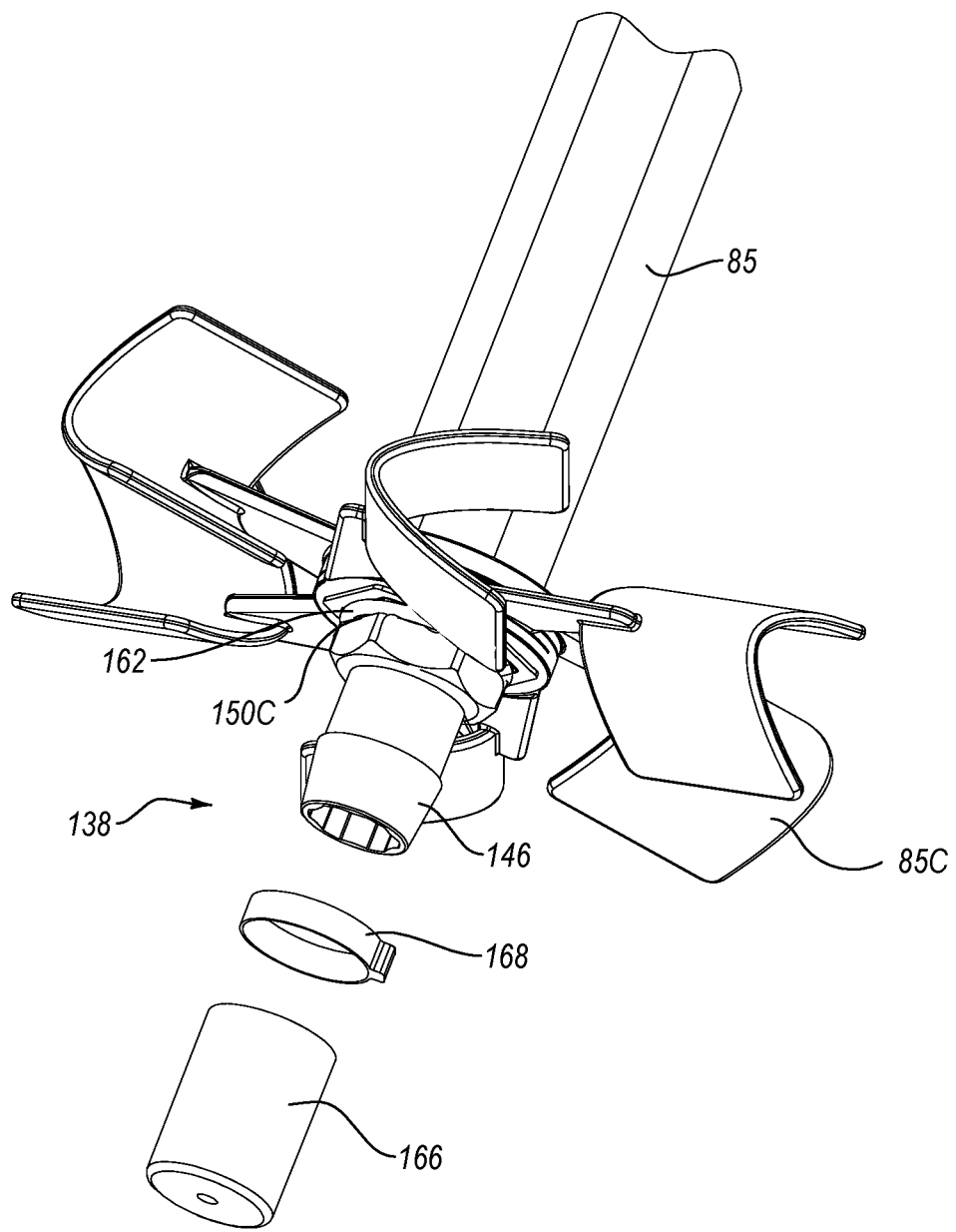
FIG. 12 is an enlarged exploded perspective view of the second end of the second tubular connector and an end cap to be received thereon, based upon FIG. 5.

FIG. 12 also shows that an end cap 166, such as made from a polymeric or elastomeric material, can be slid over stem 146 and secured by a fastener 168, such as a pull tie or crimp, so as to from a liquid tight seal at second end 138 of second tubular connector 84.

Figure 13:
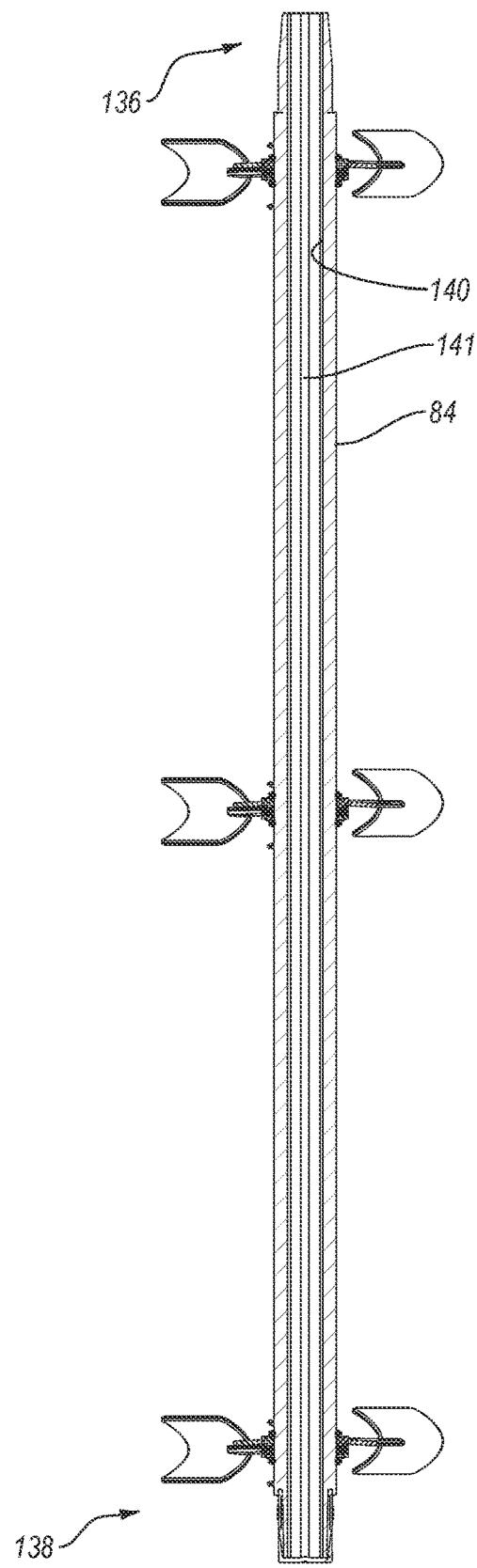
FIG. 13 is a cross sectional side view of the second tubular connector with the impellers thereon, based upon FIG. 5.

Turning to FIG. 13, interior surface 140 of second tubular connector 84 along the length thereof has a configuration that is complementary to the transverse cross section of second driver portion 114 on drive shaft 72 (FIG. 5) or is otherwise configured to engage second driver portion 114 so that when second driver portion 114 is received within passage 141 of second tubular connector 84, rotation of drive shaft 72 facilitates concurrent rotation of second tubular connector 84. For example, interior surface 140 of second tubular connector 84 and second driver portion 114 on drive shaft 72 can have complementary polygonal or other non-circular configurations.

It is appreciated that second driver portion 114 of drive shaft 72 need not engage the full length of second tubular connector 84. However, because drive shaft 72 is typically stronger than second tubular connector 84, the more length of drive shaft 72 that directly engages along the length of second tubular connector 84, the more strength is imparted to second tubular connector 84. Thus, in general, in situations where greater torque will be applied to second tubular connector 84, more length of second driver portion 114 should engage second tubular connector 84. For example, second driver portion 114 can be configured to engage at least 20% and more commonly at least 40% or 60% of the total length of second tubular connector 84. Other percentages can also be used.

During assembly, impeller assembly 78 is coupled with container 12 as discussed above. The assembly can then be sterilized, such as by irradiation, so that compartment 50 and the components therein are sterile. To facilitate shipping and storage, container 12 can be folded over at any location along the length of flexible first tubular connector 80 so as to minimize the length and size of the container assembly. During use, container 12 with impeller assembly 78 secured thereto is positioned within chamber 30 of support housing 14. Bearing assembly 82 is then removably connected to bottom surface 64 of housing 60 of drive motor assembly 59 so that hub 88 is aligned with motor mount 68. Second end 100 of drive shaft 72 is advanced down through motor mount 68, through hub 88 of bearing assembly 82, through first tubular connector 80 and finally into second tubular connector 84.

In this position, drive shaft 72 is locked to motor mount 68 with first diver portion 112 engaging hub 88 and second driver portion 114 engaging second tubular connector 84, as discussed above. As a result, rotation of motor mount 68 by drive motor 70 facilitates rotation of drive shaft 72 which in turn facilitates the concurrent rotation of hub 88, drive member 169 (i.e., first tubular connector 80 and second tubular connector 84), and impellers 85 mounted on second tubular connector 84/drive member 169. In turn, rotation of impellers 85 facilities mixing and/or suspension of the fluid within compartment 50 of container 12.

In one embodiment of the present disclosure, means are secured to impeller segments for concurrently rotating the impeller segments about a rotational axis. One example of such means is drive member 169, as discussed above, that couples with each of impeller segments 170A-C and interacts with drive shaft 72 to rotate about rotational axis 171. Other examples of such means include modifications to and alternative embodiments of tubular connectors 80 and 84 as discussed or incorporated herein. In another example of such means, tubular connectors 80 and 84 can be eliminated and replaced with a drive shaft the projects into container 12 and has impeller segment 170A-C mounted thereon. Other examples of the means for concurrently rotating impeller segment are discussed below.

Further disclosure with regard to drive motor assembly 59, bearing assembly 82, and drive shaft 72 and how these elements operate and couple together, along with alternative embodiments thereof, is disclosed in United States Patent Publication Nos. 2011-0188928 A1, published Aug. 4, 2011; 2011-0310696, published Dec. 22, 2011 and 2006-0280028, published Dec. 14, 2006 which are incorporated herein by specific reference. Further disclosure with regard to fluid mixing system 10A, including the components, assembly, use, and alternatives thereof, are also disclosed in U.S. Pat. No. 9,855,537, issued Jan. 2, 2018 which is incorporated herein in its entirety by specific reference.

Embodiments of the inventive system have a number of advantages. For example, by using second tubular connector 84 which is rigid, a plurality of impellers can be mounted thereon which significantly increases the ability to mix the fluid within container 12. This is significantly helpful in situations such as where the fluid processing system is functioning as a fermentor for growing microorganisms. This is because fermentors typically require aggressive mixing to achieve and maintain the needed gas-liquid mass transfer with the fluid to keep the microorganisms alive and thriving. The system is also advantageous in that the container assembly is easy to manufacture, scalable, and disposable after use so the no cleaning or sterilization is required. As discussed above, by using first tubular connector 80 which is flexible, the container assembly can still be folded into a relatively small volume, thereby making it easier to sterilize, ship, and store. Furthermore, the system provides an easy, modular system for attaching impellers to second tubular connector 84. For example, different systems having different numbers of impellers can be designed using the same second tubular connector 84. In addition, because all of the impellers can be mounted on second tubular connector 84, only one separate connection to first tubular connector 80 is required, thereby simplifying assembly and minimizing locations for potential contamination. Other advantages also exist.

It is appreciated that the inventive system also has a number of alternative embodiments. For example, although second tubular connector 84/drive member 169 is shown having three impellers 85 mounted thereon, in other embodiments second tubular connector 84/drive member 169 can have at least or less then 1, 2, 4, 5, 6 or more impellers 85 mounted along the length thereof. It is also appreciated that the relative lengths of first tubular connector 80 and second tubular connector 84 can be varied. For example, in some embodiments, the length of second tubular connector 84 is at least 20%, 40% or 60% of the combined total length of first tubular connector 80 and second tubular connector 84. In other embodiments, the length of first tubular connector 80 is at least 20%, 40% or 60% of the combined total length of first tubular connector 80 and second tubular connector 84. Furthermore, as previously discussed, first tubular connector 80 can be eliminated in some embodiments.

Figure 14:
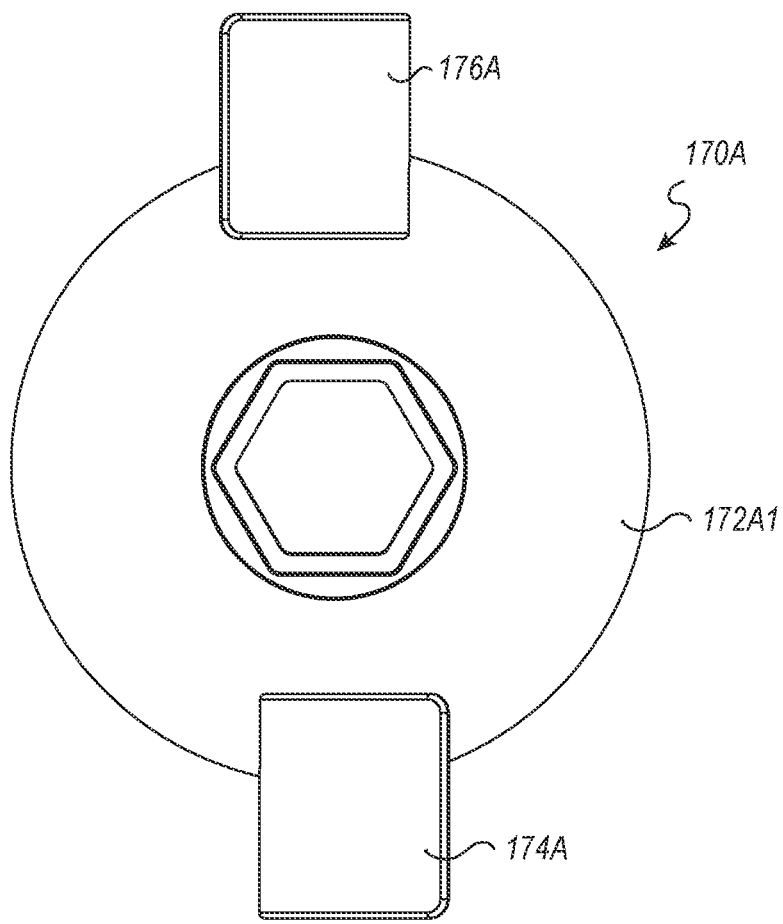
FIG. 14 is a top view of an alternative embodiment of the mount of the impeller segment shown in FIG. 10.

In still other alternative embodiments, it is appreciated that the above discussed impellers 85 and impeller segments 170 can have a variety of different configurations. For example, in FIG. 10 mount 172A is elongated. In an alternative embodiment as shown in FIG. 14, an alternative impeller segment 170A is shown having a mount 172A1 that is circular having mixing blades 174A and 176A mounted on opposing ends thereof. In still other embodiments, to reduce material costs, any desired slots, notches or openings could be formed on or through circular mount 172A1. Other forms of mounts that can support mixing blades 174 and 176 can also be used.

Figure 15:
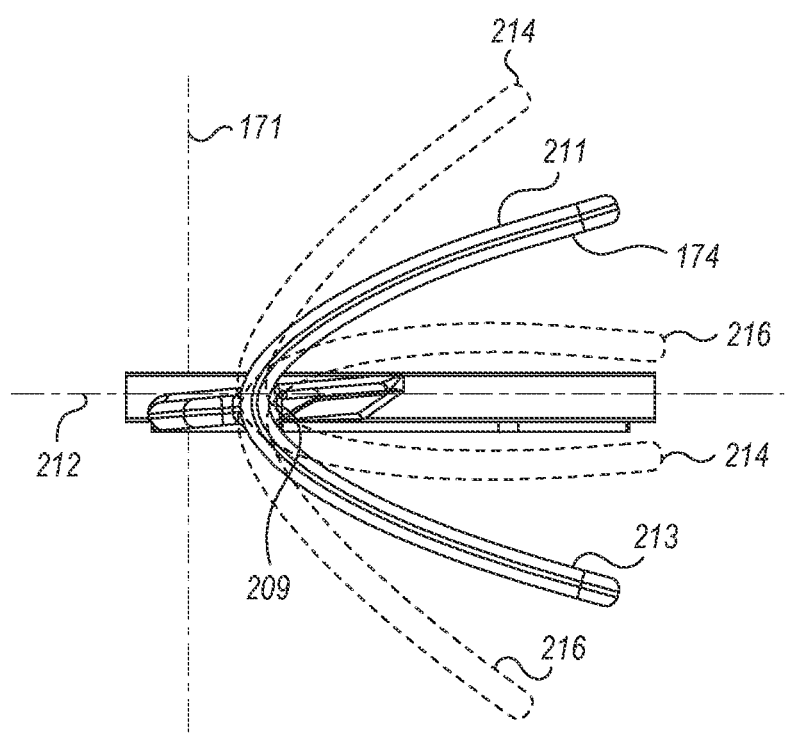
FIG. 15 is an elevated side view of the mixing blade of the impeller segment shown in FIG. 10 with the mixing blade shown in alternative orientations.

The mixing blades 174/176 can also have a variety of different configurations and orientations. For example, as depicted in FIG. 15, each mixing blade 174/176 can be orientated so that wings 211 and 213 extend symmetrically about horizontal plane 212 passing through apex 209 and extending orthogonal to axis 171. In alternative embodiments, however, mixing blades 174/176 can be tilted upward, as show by dashed lines 214, which drives fluid upward or can be tilted downward, as shown by dashed lines 216, which dives the fluid downward. In both alternatives, wings 211 and 213 have the same configuration but extend asymmetrical about plane 212.

Figure 16:
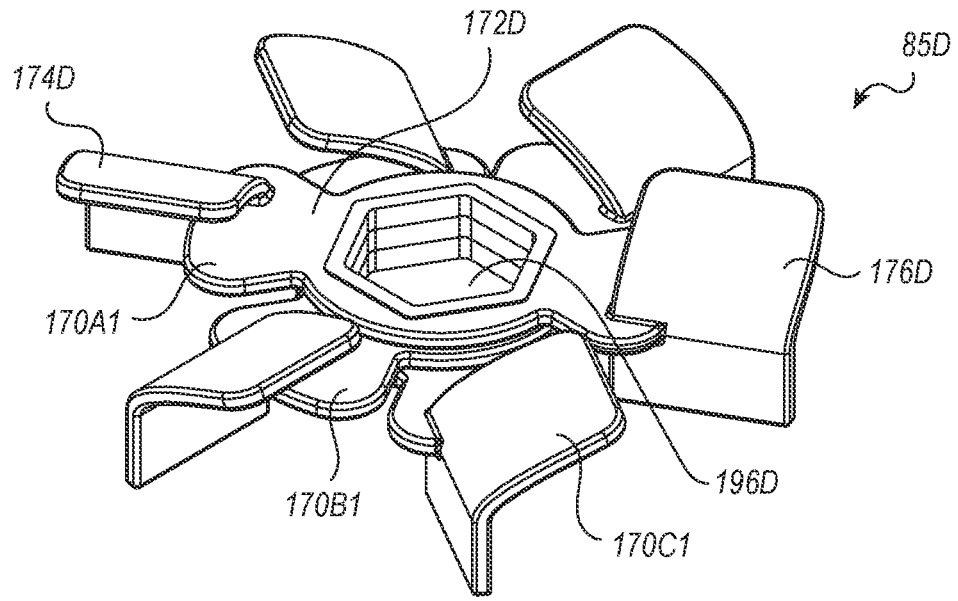
FIG. 16 is a perspective view of an alternative embodiment of the impeller shown in FIG. 8 with modified mixing blades.
Figure 17:
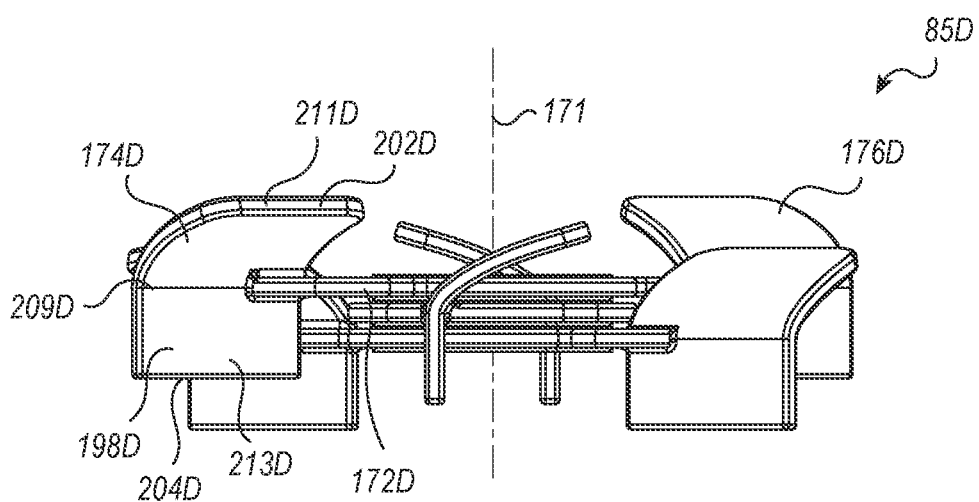
FIG. 17 is an elevated side view of the impeller shown in FIG. 16.

In still other embodiments, wings 211 and 213 of a given mixing blade 174/176 need not have the same configuration. For example, depicted in FIGS. 16 and 17 is an impeller 85D having impeller segments 170A1, 170B1 and 170C1. Impeller segment 170A1 includes mount 172D with mixing blades 174D and 176D mounted on the opposing ends thereof. However, in this embodiment, mixing blades 174D and 176D are non-symmetrical. That is mixing blade 174D has a front face 198D with an apex 209D that is disposed along a plane that passes through mount 172D and extends orthogonal to axis 171. A first wing 211D projects up and forward of apex 209D in a curved arch while a second wing 213D projects vertically down so as to extend parallel to axis 171. Thus, first wing 211D has a front face that extends in a curved arch from apex 209D to a terminal end 202D while second wing 213D has an inside face that extends planar from apex 209D to a terminal end 204D. Altering the size, configuration, and/or orientation of first wing 221D relative to second wing 213D can be used to adjust or control mixing properties such as mixing efficiency, applied shear, fluid flow path/circulation, fluid turbulence, and the like. In other embodiments, the orientations of first wing 211D and second wing 213D can be switch or first wing 211D and second wing 213D can have other configuration or project at other non-symmetrical orientations. Mixing blade 176D can have the same configuration as mixing blade 174D and each of impeller segments 170A1, 170B1 and 170C1 can have the same configurations.

Figure 18:
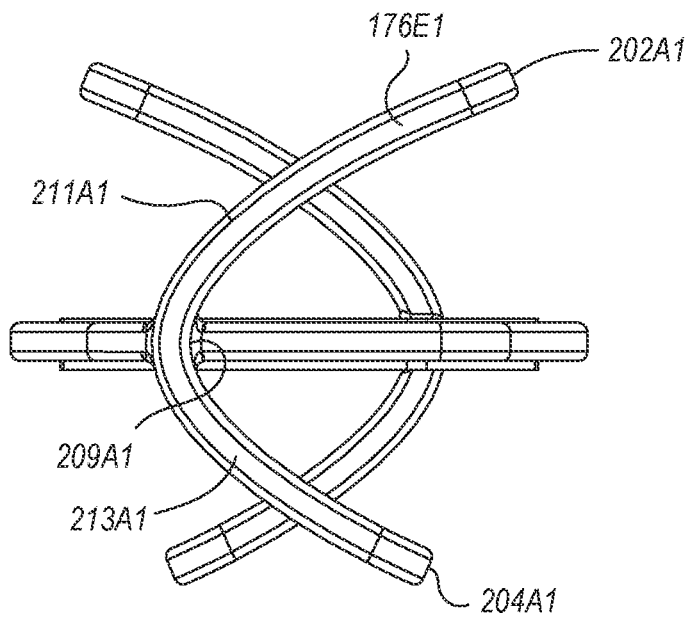
FIG. 18 is an elevated side view of an alternative embodiment of the impeller segment shown in FIG. 10 wherein the top wing of the mixing blade is longer than the bottom wing.
Figure 19:
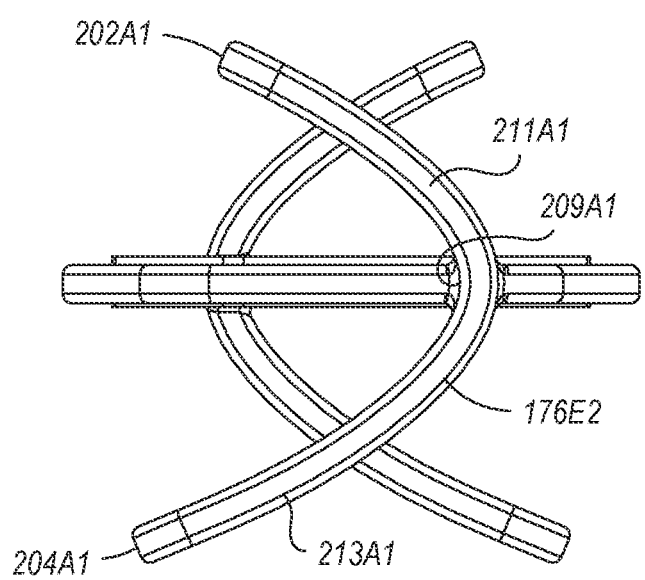
FIG. 19 is an elevated side view of an alternative embodiment of the impeller segment shown in FIG. 10 wherein the bottom wing of the mixing blade is longer than the top wing.

Turning to FIG. 18, in another alternative embodiment a mixing blade 176E1 is formed having first wing 211A1 extending from apex 209A1 to terminal tip 202A1 and second wing 213A1 extending from apex 209A1 to terminal tip 204A1. In this embodiment, the length of first wing 211A1 extending to terminal tip 202A1 is longer than the length of second wing 213A1 extending to terminal tip 204A1. This configuration helps to drive fluid downward during operation. Alternatively, FIG. 19, shows a mixing blade 176E2 formed so that second wing 213A1 extending from apex 209A1 to terminal tip 204A1 is longer than first wing 211A1 extending from apex 209A1 to terminal tip 202A1. This configuration helps to drive fluid upward during operation.

Figure 20:
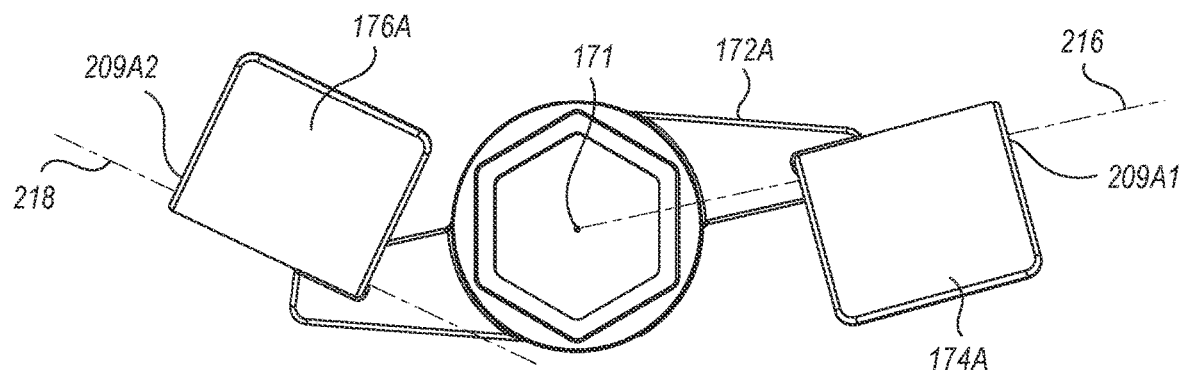
FIG. 20 is a top perspective view of the impeller segment shown in FIG. 10 wherein the mixing blades are shown being rotated into alternative orientations.

Mixing blades 174/176 can also be rotated in or out relative to the axis 171, i.e., the longitudinal axis or rotational axis of drive member 169. For example, FIG. 20 shows impeller segment 170A wherein mixing blade 174A is orientated so that a line 216 extending along apex 209A1 intersects with axis 171 passing through impeller segment 170A. Alternatively, mixing blade 176A is orientated so that a line 218 extending along apex 209A2 does not intersect with axis 171 but rather passes axis 171 at a distance spaced apart from axis 171. In alternative embodiments, mixing blades 174A and 176A can be rotated toward or away from axis 171. Rotating the mixing blade toward axis 171 pushes the fluid toward the center of container 12 (FIG. 2) during operation while rotating the mixing blade away from axis 171 pushes the fluid away from the center of container 12 during operation.

Figure 21:
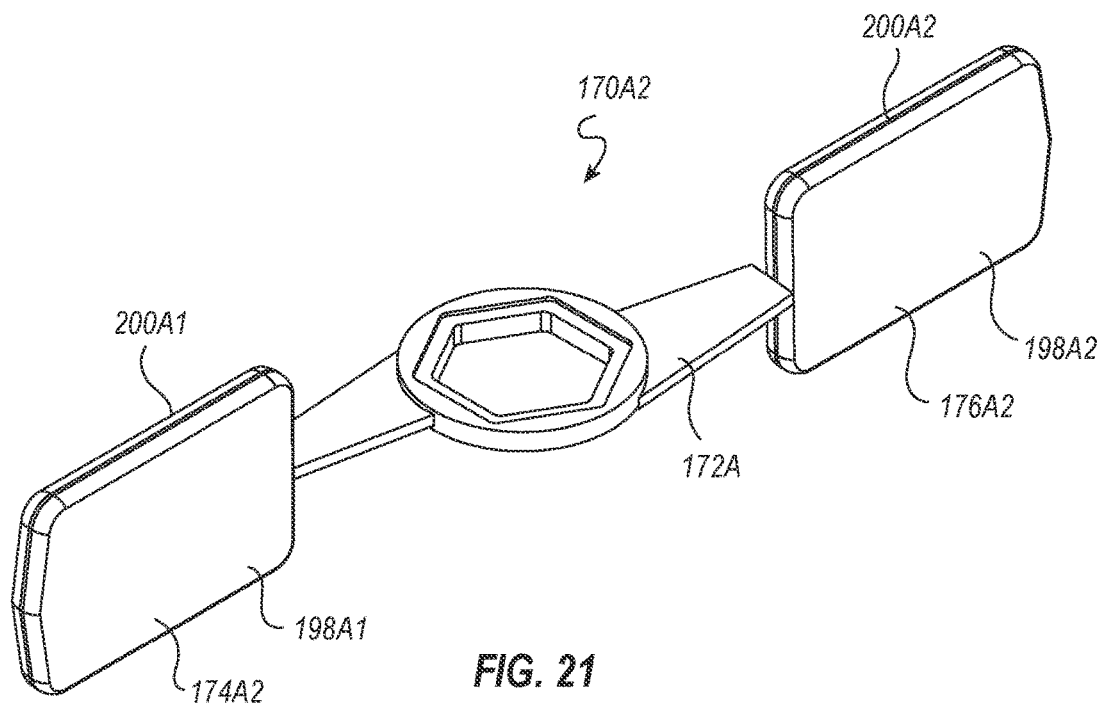
FIG. 21 is a perspective view of the impeller segment shown in FIG. 10 having mixing blades of alternative configuration.

In still other embodiments, it is appreciated that the mixing blades need not have a front face with a concave configuration. For example, depicted in FIG. 21 is an impeller segment 170A2 having mount 172A with mixing blades 174A2 and 176A2 projecting from the opposing ends thereof. In this embodiment, however, each mixing blade 174A2 and 176A2 has a front face 198A1, 198A2 and an opposing back face 200A1, 200A2 that are planar, i.e., flat along both the height and width thereof, and can be disposed in parallel alignment. Although mixing blades 174A2 and 176A2 may have a decreased mixing efficiency relative to parabolic mixing blades, such a mixing blade configuration may have other benefits, such as controlling flow circulation in some application or have a reduced production cost. In still other embodiments, the mixing blades can have other configurations, such as the configuration of other mixing blades used on impellers for mixing fluids.

Figure 22:
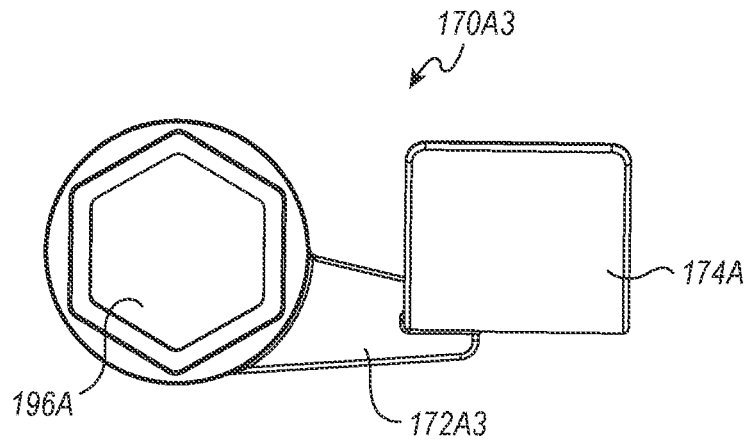
FIG. 22 is a top plan view an alternative impeller segment having only a single mixing blade.

In the embodiment previously shown in FIGS. 8 and 9, each impeller segment 170A-C has two mixing blades 174 and 176 mounted thereon. However, in other embodiments, impeller segments can be formed with only one mixing blade or three mixing blades. For example, depicted in FIG. 22 is an impeller segment 170A3 having a mount 172A3 with a single mixing blade 174A mounted thereon. Mount 172A3 and mixing blade 174A can have any of the configurations or alternatives as discussed herein. During use, the desired number of impeller segments 170A3 can be used depending upon the number of mixing blades desired. For example, where opening 196A passing through mount 172A3 again has a hexagonal configuration, six impeller segments 170A3 can be used where each impeller segment 170A3 is rotated 60° relative to the prior when mounting on second tubular connector 84/drive member 169. As such, the resulting impeller has six mixing blades that are each equally radially spaced apart. In other embodiments where only three mixing blades are needed, three impeller segments 170A3 can be used where each impeller segment 170A3 is rotated 120° relative to the prior when mounting on second tubular connector 84/drive member 169. Other numbers of impeller segments 170A3 can also be used.

Figure 23:
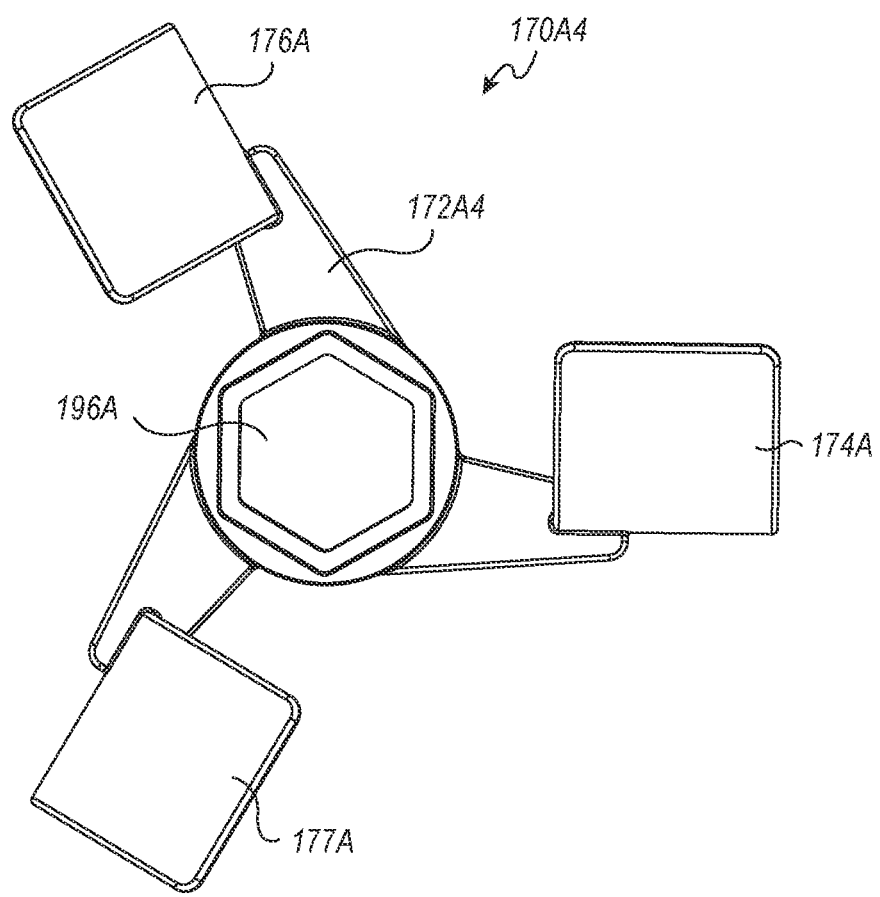
FIG. 23 is a top plan view an alternative impeller segment compared to FIG. 5 having three mixing blades.

FIG. 23 shows an impeller segment 170A4 having a mount 172A4 with three spaced apart mixing blades 174A, 176A, and 177A mounted thereon. Again, the mount and mixing blades of impeller segment 170A4 can have any of the configurations or alternatives as discussed herein. Impeller segment 170A4 can be used with a second impeller segment having the same configuration. During use, the second impeller segment is rotated relative to the first impeller segment when mounting on second tubular connector 84, such as 30° when opening 196A is a hexagon. Accordingly, the resulting impeller can again have six equally spaced apart mixing blades. In all of the embodiments disclosed herein, it is appreciated that any desired number of impeller segments can be used depending on the intended application. For example, an impeller can be formed having at least or less than 2, 3, 4, 5, 6 of more impeller segments 170A4. Likewise, impeller 85A previously shown in FIGS. 7 and 8, could be formed with at least or less than 2, 4, 5, 6, or more impeller segments 170.

Returning to FIG. 10, in one embodiment, first terminal end 202A1 of first mixing blade 174A extending between inside edge 206A1 and outside edge 208A1 can taper so as to terminate at a sharpened or rounded first terminal edge 203A1 that also extends between inside edge 206A1 and outside edge 208A1. The tapering of first terminal edge 203A1 allows first terminal edge 203A1 to more efficiently cut through the liquid being mixed so as to improve mixing efficiency.

In one embodiment, the tapering of first terminal end 202A1 can be constant between inside edge 206A1 and outside edge 208A1 so that first terminal edge 203A1 has a constant thickness between front face 198A1 and back face 200A1 along the length between inside edge 206A1 and outside edge 208A1. However, in this embodiment, aggressive tapering of first terminal end 202A1 can result in a sharpened outside corner 205A1 formed at the intersection between first terminal end 202A1 and outside edge 208A1. Sharpened outside corner 205A1 runs the risk of potentially puncturing or otherwise damaging container 12 (FIG. 2) when container 12 is collapsed against impellers 85, such as during assembly, shipping, storage, and/or installation prior to use. In other embodiments, however, the tapering of first terminal end 202A1, and thus the thickness of first terminal edge 203A1, can vary at one or more points between inside edge 206A1 and outside edge 208A1 so as to eliminate or mitigate the risk associated with outside corner 205A1.

Figure 24:
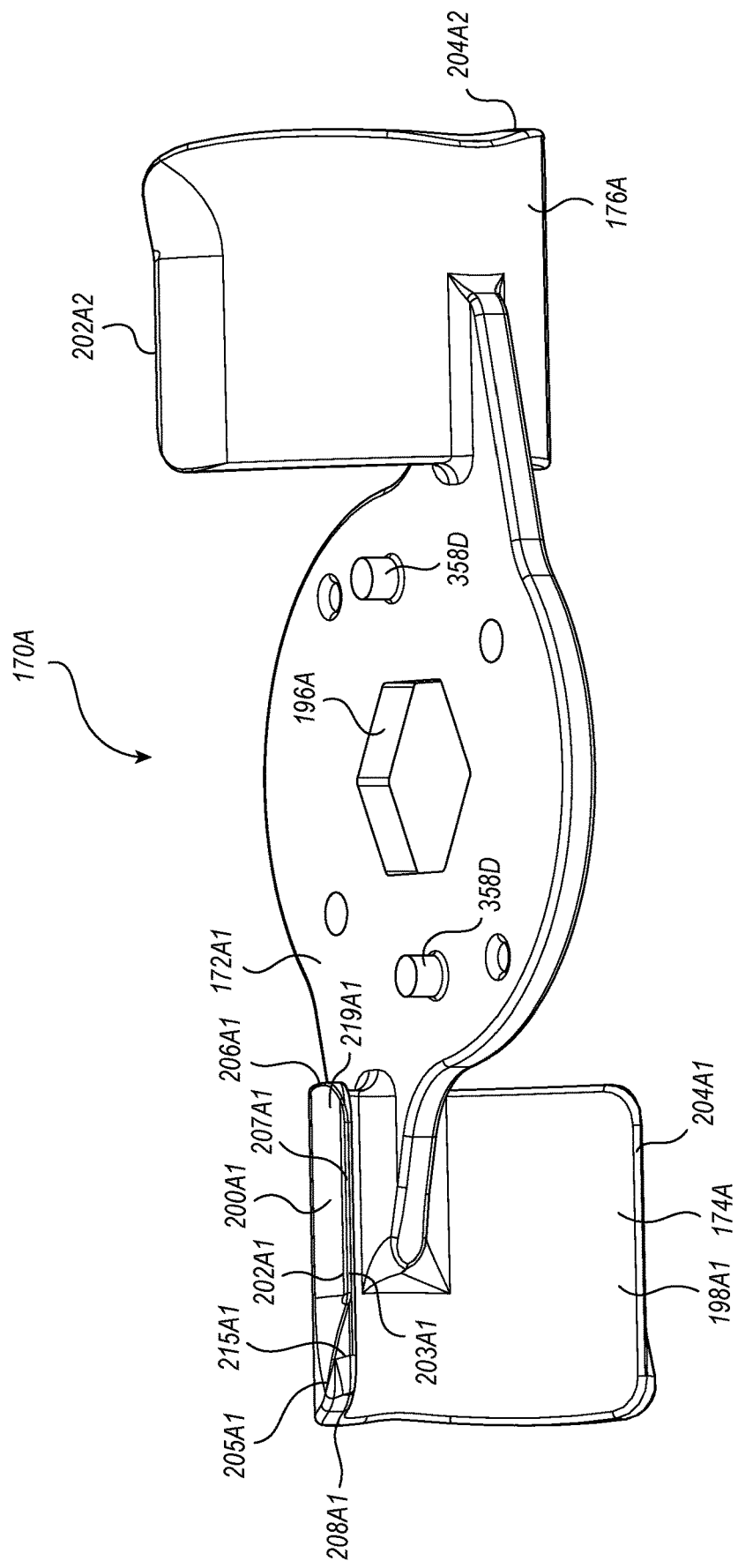
FIG. 24 is a perspective view of an alternative impeller segment wherein a taper of the terminal ends of each of the blades varies at points along the width.

For example, depicted in FIG. 24 is a further modified version of impeller segment 170A that includes rounded first mount 172A1 having first mixing blade 174A and second mixing blade 176A mounted thereon. First mixing blade 174A includes first terminal end 202A1 that extends between inside edge 206A1 and outside edge 208A1. In this embodiment, however, first terminal end 202A1 does not have a constant taper that extends between inside edge 206A1 and outside edge 208A1 but rather has a taper that varies at one or more points along the length thereof. More specifically, first terminal end 202A1 includes a first terminal end portion 207A1 that extends to inside edge 206A1 and a second terminal end portion 215A1 that extends from first terminal end portion 207A1 to outside edge 208A1.

In this embodiment, first terminal end portion 207A1 is more tapered than second terminal end portion 215A1. Expressed in other terms, first terminal end 202A1 can taper or otherwise extend to a first terminal edge 203A1 that extends between inside edge 206A1 and outside edge 208A1. First terminal end 202A1 and first terminal edge 203A1 have a thickness that extends front face 198A1 and back face 200A1. The minimal thickness of first terminal end 202A1/first terminal edge 203A1 of first terminal end portion 207A1 is less than a minimal thickness of first terminal end 202A1/first terminal edge 203A1 of second terminal end portion 215A1. Likewise, the maximum thickness of first terminal end 202A1/first terminal edge 203A1 of second terminal end portion 215A is greater than a maximum thickness of first terminal end 202A1/first terminal edge 203A1 of first terminal end portion 207A1. In one embodiment, second terminal end portion 215A1 extending from outside edge 208A1 can comprise less than 40%, 30%, 20%, 10%, or 5% of the length of first terminal end 202A1. Likewise, first terminal end portion 207A1 extending from inside edge 206A1 can comprise at least or less than 50%, 60%, 70%, 80%, or 90% of the length of first terminal end 202A1 or can be in a range between any two of the listed percentages.

In one embedment the thickness of first terminal end 202A1/first terminal edge 203A1 at outside corner 205A1 can be greater than a thickness of first terminal end 202A1/first terminal edge 203A1 at a center location between inside edge 206A1 and outside edge 208A1 and/or can be greater than a thickness of first terminal end 202A1/first terminal edge 203A1 at an inside corner 219A1 formed at the intersection between first terminal end 202A1 and inside edge 206A1.

It is understood that second terminal end 204A1 of first mixing blade 174A and terminal ends 202A2 and 204A2 of second mixing blade 176A can have the same tapering configuration and alternatives as discussed above with regard to first terminal end 202A1. As such, all of the above disclosure with regard to the tapering and alternatives of first terminal end 202A1 is also applicable to terminal ends 204A1, 202A2 and 204A2 and like reference numbers can be used to identify like elements.

It is appreciated that each of the above features of the different impeller segments can be mixed and matched as desired to form a variety of different configurations of impellers to achieve a variety of different mixing properties. For example, in one embodiment of an impeller, all of the impeller segments can be identical. In another embodiment, by using any of the above alternatives, each or at least one of the impeller segments can be different from the others using any of the alternatives discussed above. For example, the mixing blades on one impeller segment could be designed to push fluid downward or inward while mixing blades on another impeller segment could be designed to push fluid upward or outward. Thus, by combining impeller segments of different configurations, mixing properties can be tailored for specific applications. In still other embodiments, the blades on a single impeller segment can be the same or different.

Figure 25:
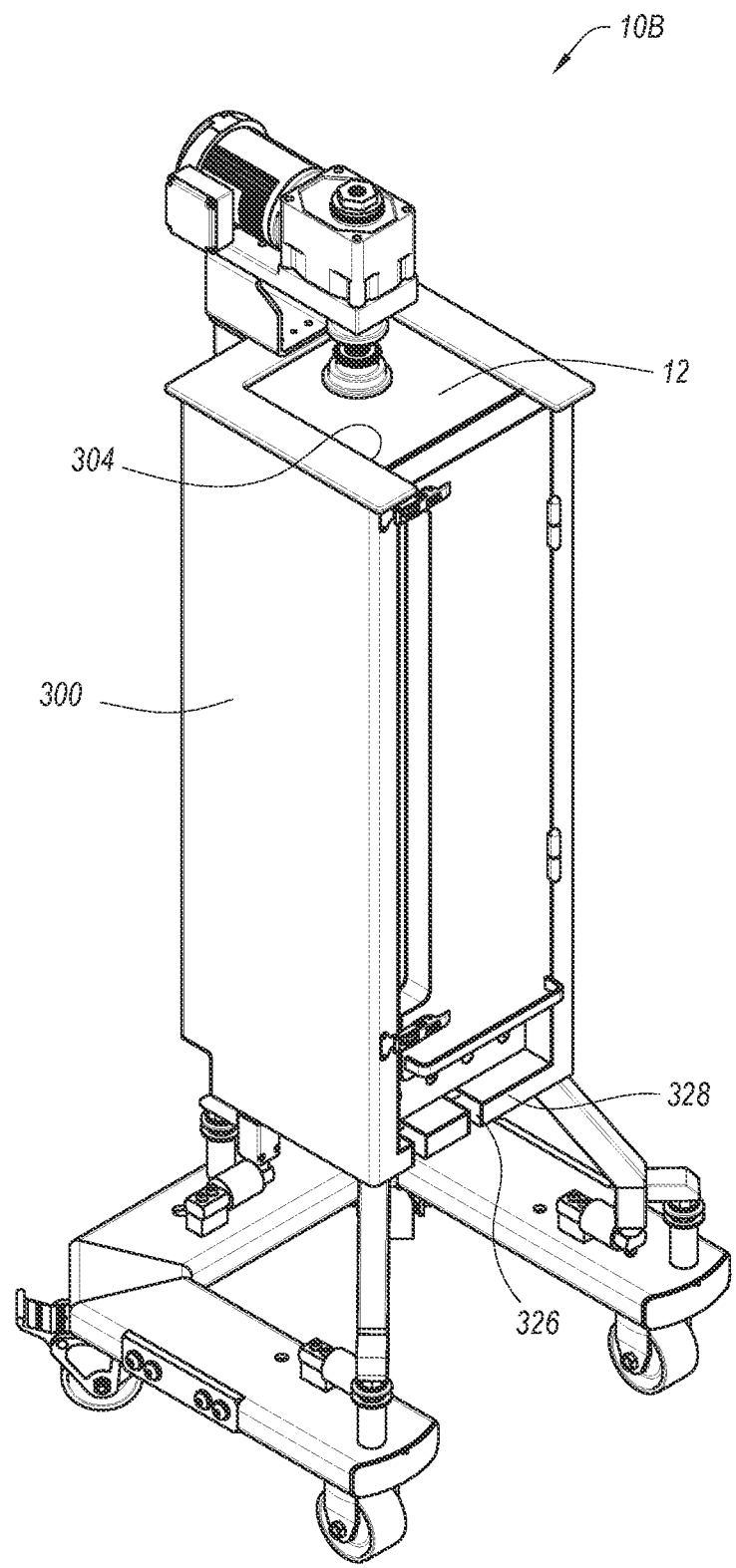
FIG. 25 is a perspective view of an alternative fluid mixing system compared to FIG. 1.

In still other embodiments, it is appreciated that the modular impellers and the alternatives thereof disclosed herein can be used with fluid mixing systems other than fluid mixing system 10A discussed above. For example, depicted in FIG. 25 is an alternative fluid mixing system 10B incorporating features of the present disclosure which can incorporate modular impellers. Like elements between mixing system 10A and 10B are identified by like reference numbers. In general, mixing system 10B comprises container 12 that is disposed within a compartment 304 of a rigid support housing 300.

Figure 26:
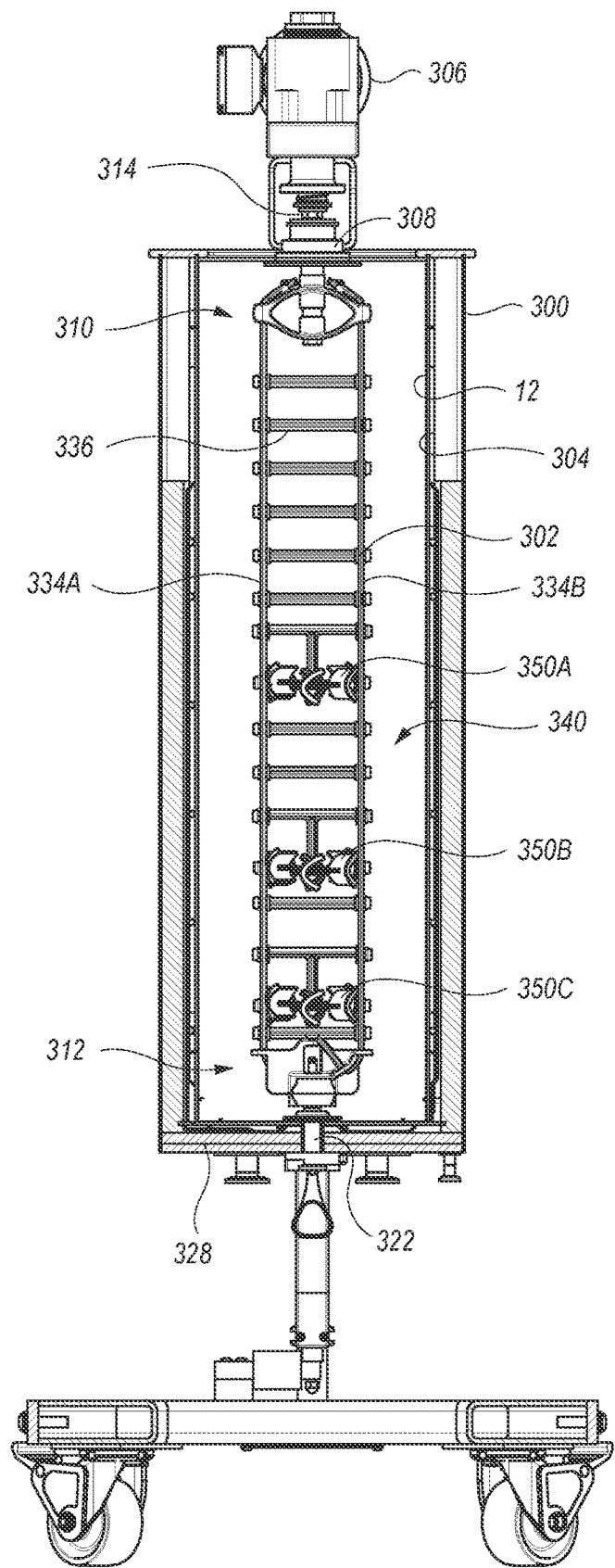
FIG. 26 is an elevated, partial cross sectional view of the fluid mixing system shown in FIG. 25.
Figure 27:
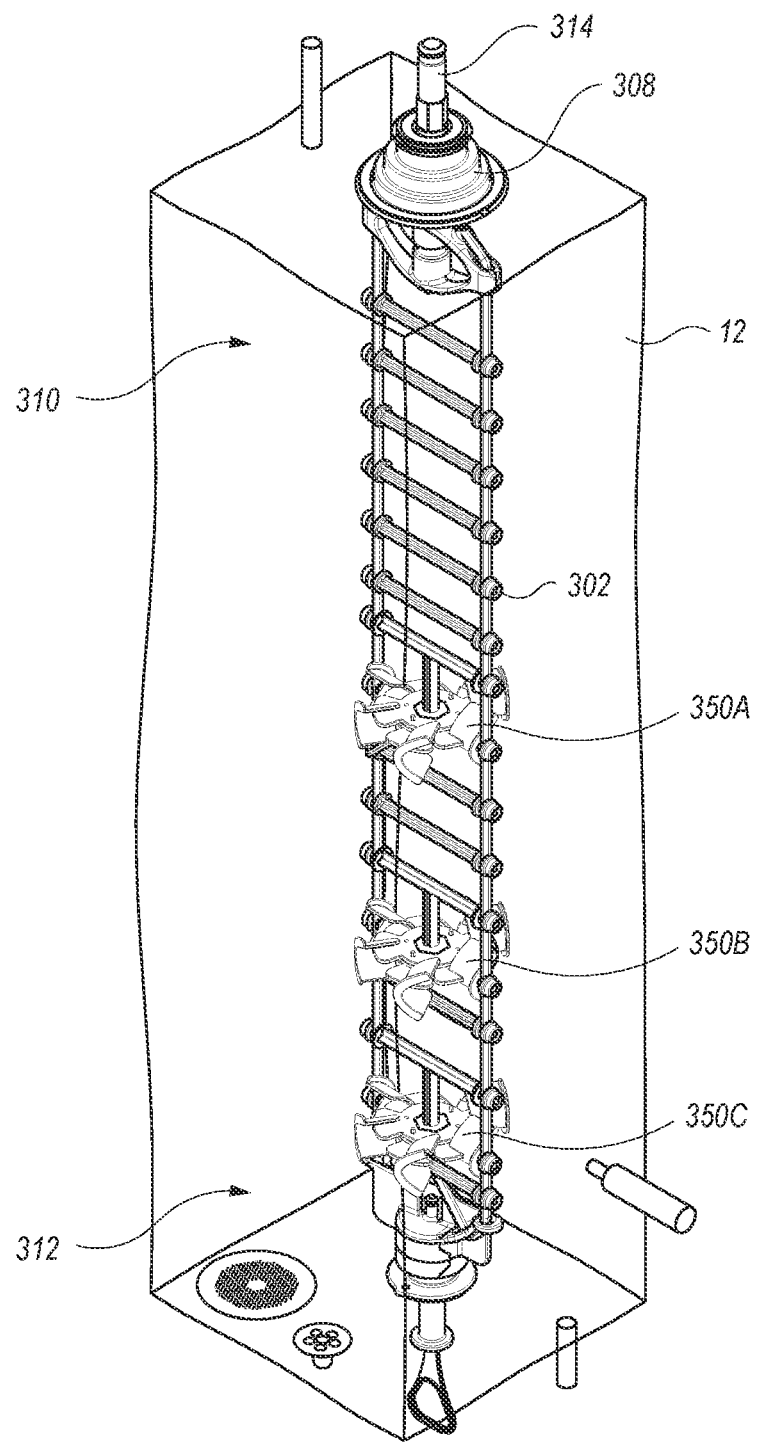
FIG. 27 is a perspective view of the container and mixer assembly of the fluid mixing system shown in FIG. 25.

With reference to FIG. 26, mixing system 10B further comprises a motor assembly 306 that is mounted on support housing 300, a first bearing assembly 308 secured to a top end of container 12, and a mixer assembly 302 disposed with container 12. Mixer assembly 302 has a first end 310 disposed at an upper end of container 12 and an opposing second end 312 disposed at a lower end of container 12. A drive shaft 314, as shown in FIG. 27, passes through first bearing assembly 308 and has a first end releasably connected to motor assembly 306 (FIG. 26) and an opposing second end connected to first end 310 of mixer assembly 302.

Figure 28:
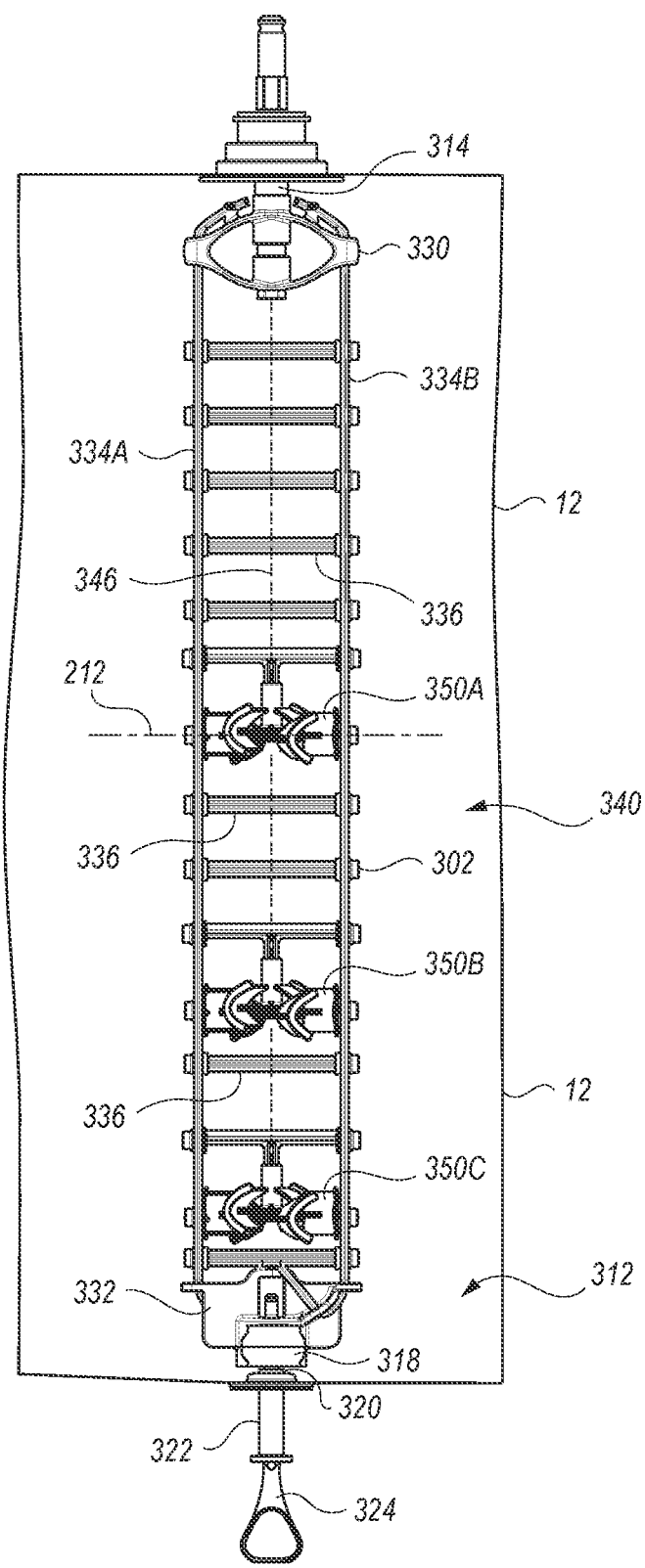
FIG. 28 is an elevated side view of the container and mixer assembly shown in FIG. 27.

As better shown in FIG. 28, a sealing flange 316 is secured to a bottom end of container 12. Disposed withing container 12 and secured to second end 312 of mixing assembly is 302 is a second bearing assembly 318. A thrust pin 320 has a first end coupled to bearing assembly 318 and an opposing second end coupled to sealing flange 316. Second bearing assembly 318 freely rotates on the first end of thrust pin 320. A retaining post 322 downwardly extends from sealing flange 316 outside of container 12 and has a handle 324 mounted thereon.

During use, as shown in FIG. 26, container 12 is disposed within compartment 304 of rigid support housing 300 with retaining post 322 being disposed and secured within a slot 326 (FIG. 25) passing through a floor 328 of rigid support housing 300. The first end of drive shaft 314 is connected to motor assembly 306. In this configuration, operation of motor assembly 306 rotates drive shaft 314 which in turn rotates mixer assembly 302 within container 12.

With reference to FIG. 28, mixer assembly 302 comprises a first retainer 330 secured to the second end of drive shaft 314 within the upper end of container 12 and a second retainer 332 secured to second bearing assembly 318 within the lower end of container 12. A first drive member 334A and a second drive member 334B extend between first retainer 330 and second retainer 332 so that at least a portion of drive members 334A and 334B extending between retainers 330 and 332 are laterally spaced apart. In the depicted embodiment, the entire length of drive members 334A and 334B extending between retainers 330 and 332 are laterally spaced apart.

Each drive members 334A and 334B comprises a flexible line. Drive members 334A and 334B can comprise two separate and discrete members or can comprise separate portions of one continuous member. Drive members 334A and 334B can be made from a variety of different flexible materials and can have different configurations. By way of example and not be limitation, in one embodiment drive members 334A and 334B can be made from a braded or woven material such as cable, cord or rope. The braded material can be made from a plurality of different strands that are comprised of metal, polymer, composite or other materials that have desired strength and flexibility properties and can be sterilized. For example, the strands can be made from metal like stainless steel or a polymer like ultra-high molecular weight polyethylene (UHMwPE) such as that sold under the trademark DYNEEMA. In other embodiments, drive members 334A and 334B can be made from a flexible tube, a single solid core line, a linkage, such as a chain or a linkage of universal joints, or other flexible or hinged members made from any of the above discussed materials. Drive members 334A and 334B can have a transverse cross section that is circular oval, oblong, rectangular, angled, irregular, polygonal or have other configurations. For example, in one embodiment drive members 334A and 334B can be in the form of a flat strap or strip. The diameter of drive members 334A and 334B is in part dependent upon the materials used to make the drive members and the size of the system. However, in some embodiments, the maximum or minimum diameter of each drive member 334A and 334B can be greater than, less than, or equal to 2 mm, 4 mm, 6 mm, 8 mm, 10 mm, 15 mm, 20 mm, or 30 mm, or 40 mm or in a range between any two of the foregoing. Other dimensions can also be used.

As used herein, the term "diameter," whether in reference to the size of a drive line or other component (e.g., an opening), is not limited to the measurement of circular or spherical components. Rather, whether circular, oval or oblong, rectangular, polygonal, angled or jagged, or a combination thereof, the diameter of the component refers to a (cross-sectional) measurement between opposing sides and/or the (maximum or minimum) distance between the opposing sides.

In one embodiment, at least a portion of the length of each drive member 334 is sufficiently flexible so that the flexible portion of each drive member 334 can be twisted under torsion about a longitudinal axis of each drive member 334 over an angle of at least 15°, 25°, 45°, 90°, 180°, 360°, 720° or more without plastic deformation of drive member 334. In other embodiments, at least a portion of the length of each drive member 334 is sufficiently flexible so that the flexible portion of each drive member 334 can be bent or folded relative to a linear longitudinal axis of drive member 334 over an angle of at least 15°, 25°, 45°, 90°, 135°, 180°, 270°, or 360° or more without plastic deformation of drive member 334. Expressed in other terms, each drive member 334 or the flexible portion of each drive member 334 can have a bend radius wrapped 180° without plastic deformation in a range between about 2 cm to about 100 cm with about 6 cm to about 80 cm, about 10 cm to about 60 cm, or about 10 cm to about 40 cm being more common. Other flexibilities can also be used. As noted above, the entire length of each drive member 334 need not be flexible. For example, a percentage of the entire length of each drive member 334, such as at least or not to exceed 30%, 40%, 50%, 60%, 70%, 80%, 90% or more of drive member3 334, could have the above flexible properties while the remainder is rigid or at least more rigid. In other embodiments, the entire length of drive member 334 can have the desired flexible properties.

With reference to FIG. 28, rungs 336 are used in part to maintain at least portions of drive members 334A and 334B in laterally spaced apart positions during operation of fluid mixing system 10B. Because rungs 336 are typically under compression between drive members 334A and 334B during operation, rungs 336 are typically more rigid than drive members 334A and 334B and are typically made from a metal, polymer, ceramic, composite or other material. Rungs 336 are thus typically made form a different material than drive members 334. Each rung 336 has a first end coupled to drive member 334A and an opposing second end coupled to drive member 334B.

Figure 30:
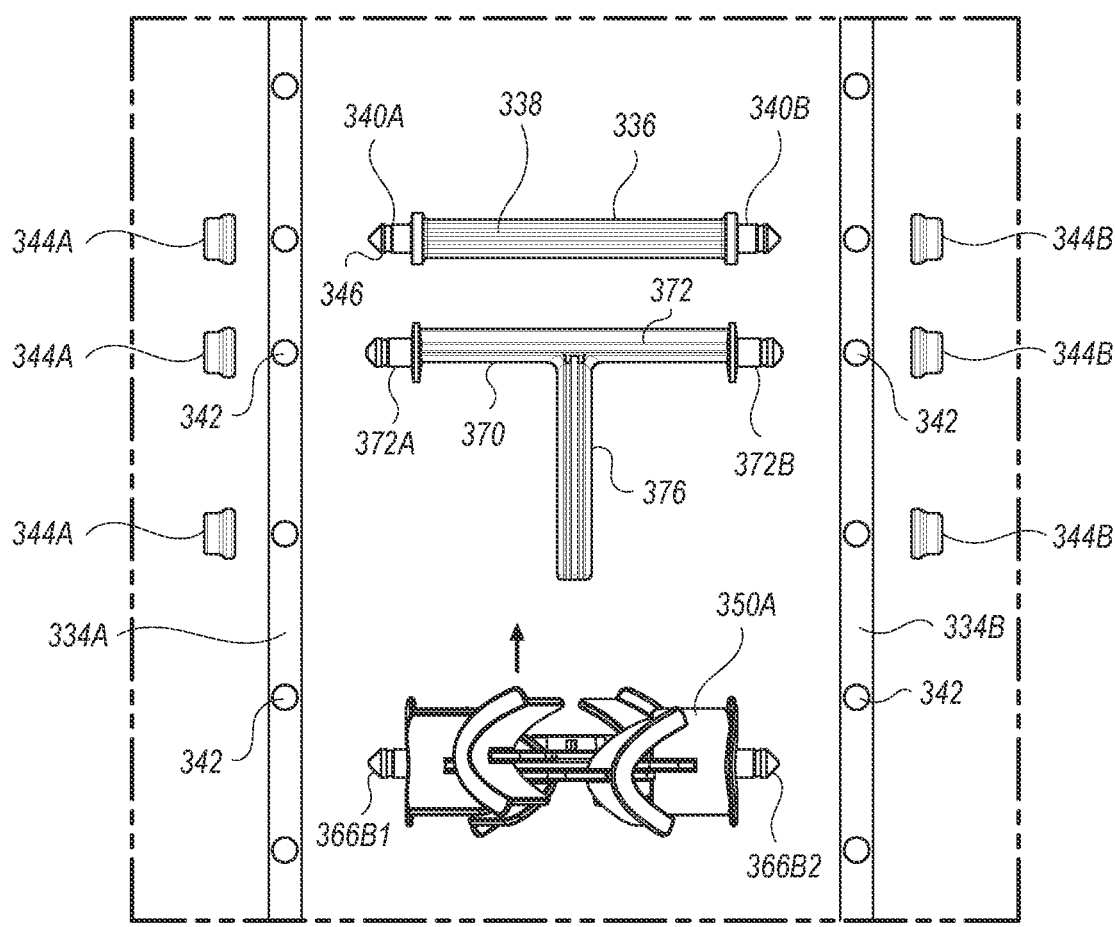
FIG. 30 is a partial exploded view of the assembly shown in FIG. 29.

More specifically, as depicted in FIG. 30, each rung 336 comprises an elongated brace 338. A first mounting stem 340A outwardly projects from a first end of brace 338 while a second mounting stem 340B outwardly projects from an opposing second end of brace 338. Each mounting stem 340A and 340B is configured to couple with a corresponding cap 344A and 344B, respectively. For example, each mounting stem 340A and 340B is shown having an annular barb 346 so that each mounting stem 340A and 340B can securely snap fit into corresponding caps 344A and 344B. In other embodiments, alternative fastening mechanisms can be used to couple mounting stems 340 to caps 344. For example, they can be coupled together by threaded engagement, press fit connection, clamping, welding or by using other techniques.

Each drive member 334A and 334B has a plurality of longitudinally spaced apart holes 342 passing therethrough. Holes 342 are positioned so that when drive members 334A and 334B are vertically aligned, holes 342 on drive members 334A and 334B are horizontally aligned. During assembly, mounting stem 340A of a given brace 338 is passed through a hole 342 on drive member 334A. Cap 344A is then secured to mounting stem 340A so that the first end of brace 338 is securely fixed to drive member 334A. Similarly, mounting stem 340B of brace 338 is passed through a hole 342 on drive member 334B. Cap 344B is then secured to mounting stem 340B so that the second end of brace 338 is securely fixed to drive member 334B. The process is then repeated for multiple rungs 336 at spaced apart locations along the length drive members 334A and 334B as shown in FIG. 28.

Figure 31:
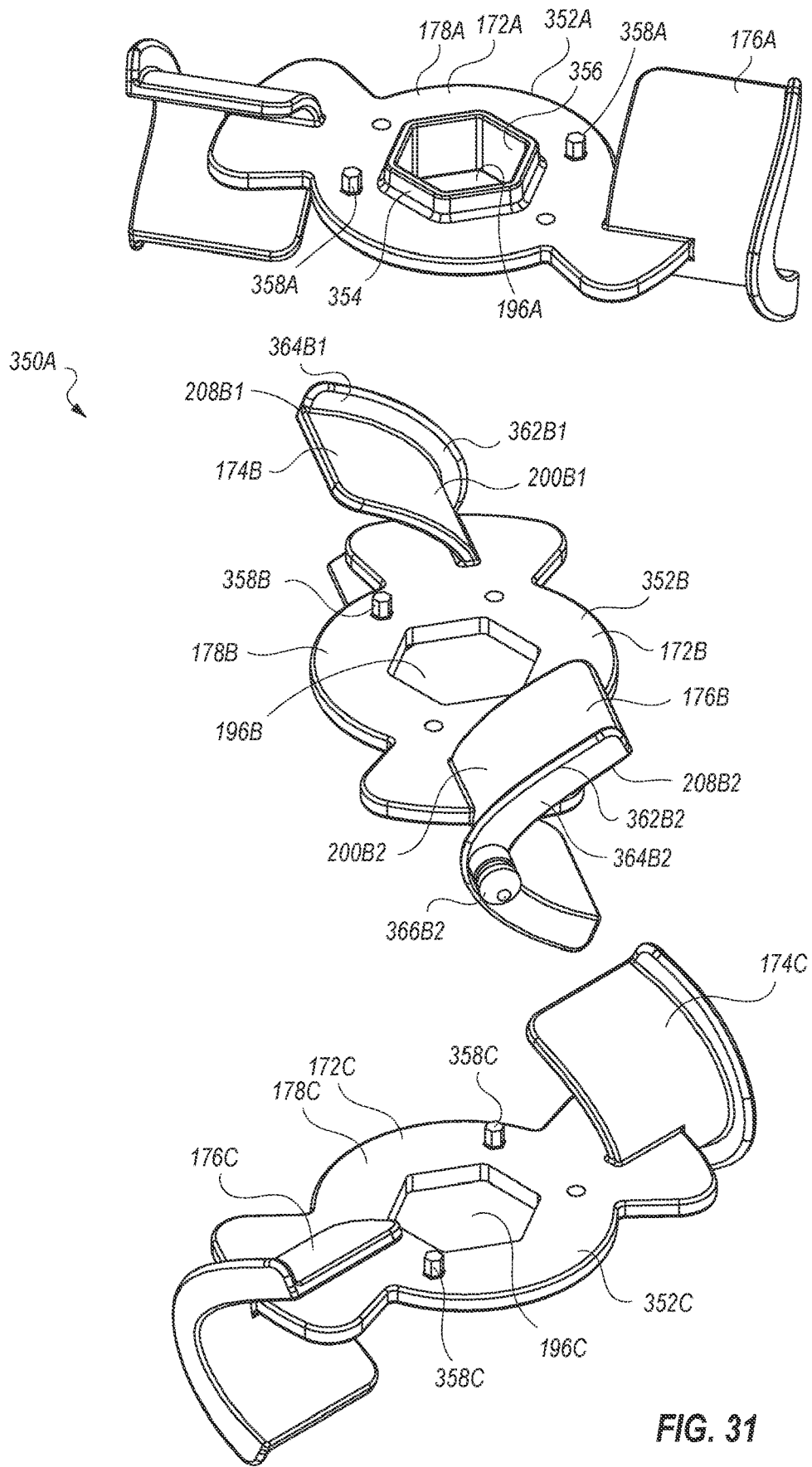
FIG. 31 is an exploded top perspective view of the impeller shown in FIG. 30.

As also shown in FIG. 28 a plurality of impellers 350A-C are secured to and extend between drive member 334A and 334B at spaced apart locations along drive member 334A and 334B. Impeller 350A has substantial similarities to impeller 85A and like elements are identified by like reference characters. Turning to FIG. 31, impeller 350A comprises impeller segments 352A, 352B and 35C. Impeller segment 352A includes mount 172A having opening 196A extending therethrough and mixing blades 174A and 176A projecting from the opposing ends of mount 172A. All of the previous discussion, elements, methods and alternatives relating to mount 172A and mixing blades 174A and 176A of impeller 85A of mixing system 10A and are also applicable to impeller 350A of mixing system 10B. However, impeller segment 352A also has some additional elements relative to impeller segment 170A. Specifically, although not required, impeller segment 352A also includes a sleeve 354 projecting from top face 178A of mount 172A so as to encircle opening 196A. Sleeve 354 encircles a passage 356 that is aligned with and has the same configuration as opening 196A. As discussed below in more detail, sleeve 354 assists in stabilizing impeller 350A during operation.

Figure 29:
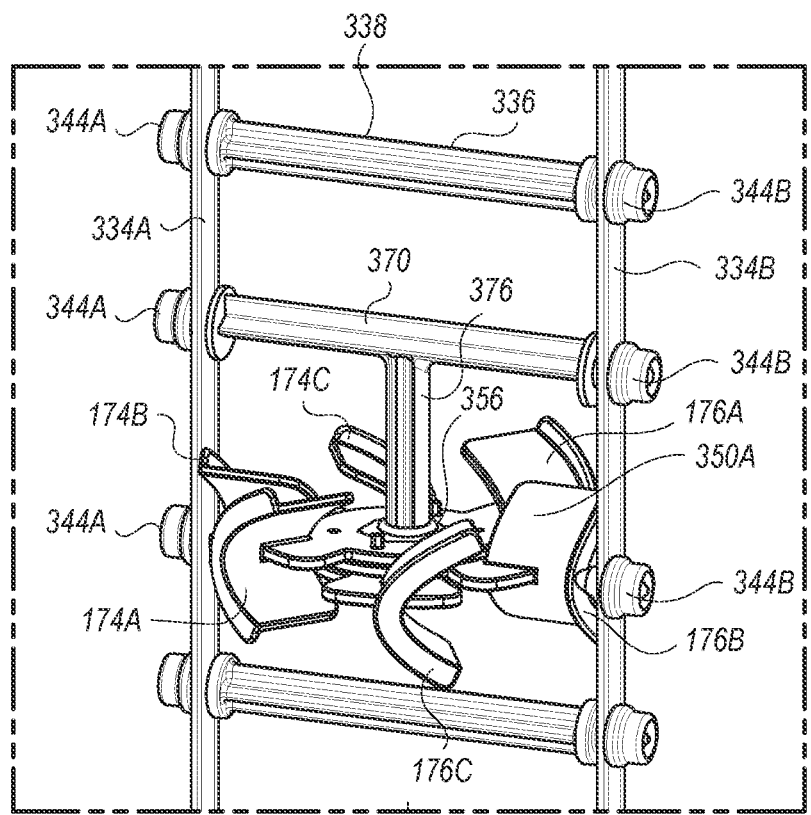
FIG. 29 is an enlarged perspective view of a portion of the mixer assembly shown in FIG. 27 showing the impeller.
Figure 32:
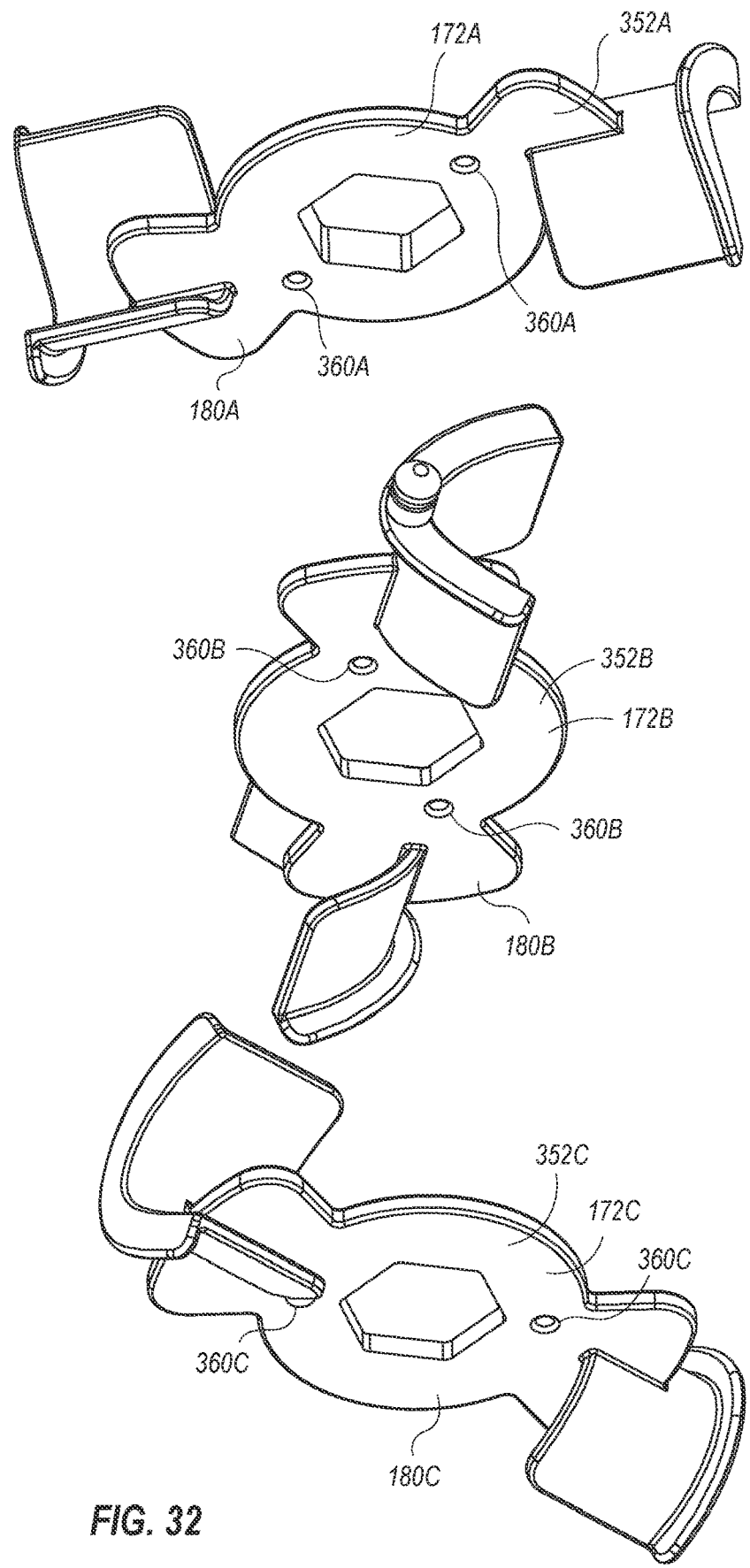
FIG. 32 is an exploded bottom perspective view of the impeller shown in FIG. 30.

Impeller segment 352B likewise includes mount 172B having opening 196B extending therethrough and mixing blades 174B and 176B projecting from the opposing ends of mount 172B. Impeller segment 352C likewise includes mount 172C having opening 196C extending therethrough and mixing blades 174C and 176C projecting from the opposing ends of mount 172C. Again, all of the previous discussion, elements, methods and alternatives relating to mounts 172B and 172C, mixing blades 174B and 174C and mixing blades 176B and 176C of impeller 85A of mixing system 10A are also applicable to impeller 350A of mixing system 10B. However, impeller 350A also includes means for securely fixing impeller segments 352A, 352B and 352C together. By way of example and not by limitation, each of mounts 172A-C are formed with spaced apart posts 358A-C upwardly projecting from top faces 178A-C, respectively. Likewise, as shown in FIG. 32, each mount 176A-C is formed with spaced apart holes 360A-C formed on bottom surfaces 180A-C, respectively. Posts 358 are configured so that they can be press fit into holes 360, such as through the use of a mechanical press, so as to produce a secure friction tight engagement between impeller segments 352A, 352B and 352C. Specifically, posts 358C of impeller segment 352C can be press fit into holes 360B of impeller segment 352B while posts 358B of impeller segment 352B can be press fit into holes 360A of impeller segment 352A so as to securely fix impeller segments 352A-C together. In alternative embodiments, posts 358 can be configured to be manually press fit into holes 360 so as to secure together impeller segments 352. It is appreciated that posts 358 and holes 360 are properly positioned so that when impeller segments 352A-C are secured together, mixing blades 174A-C and 176A-C are all evenly spaced apart as depicted in FIG. 29. In the depicted embodiment, posts 358 have a polygonal transverse cross section. In alternative embodiments, posts 358 can have a cylindrical configuration, such as post 358D shown in FIG. 24, or can have other configuration. Holes 360 are configured to receive corresponding posts 358 so as to achieve a friction tight engagement therebetween. Holes 360 can have a circular, polygonal or other transverse cross section. In one embodiment, the transverse cross section of holes 360 can be the same shape as the transverse cross section of the corresponding post 358. In other embodiments, the transverse cross section of holes 360 can have a different shape than the transverse cross section of the corresponding post 358. For example, posts 358 can have a polygonal transverse cross section while holes 360 have a circular transverse cross section. Other combinations can also be used to achieve the desired friction fit.

In one embodiment, posts 358 and holes 360 can be configured so that impeller segment 352A-C can only be assembled in one configuration. For example, impeller segments 352A-C can be configured so that only posts 358C of impeller segment 352C can be received in friction fit within holes 360B of impeller segment 352B and only posts 358B of impeller segment 352B can be received in friction fit within holes 360A of impeller segment 352A. For example, this can be accomplished by having posts 358C and holes 360B a different size, shape, and/or relative position than posts 358B and holes 360A. This design helps to ensure that impellers 350 are always properly assembled for proper operation.

It is appreciated that there are a variety of other mechanisms that can be used to securely fix impeller segments 352A, 352B and 352C together. For example, impeller segments 352A-C can be secured together by snap-fit connection, screws, bolts, clips, clamps, welding, adhesive, threaded coupling and other conventional techniques.

Impeller segment 352B also differs from impeller segment 170B in that an elongated brace 362B1 projects from back face 200B1 of mixing blade 174B along outside edge 208B1. Brace 362B1 has an outside face 364B1 facing away from mount 172B. A mounting stem 366B1 outwardly projects from outside face 364B1. Mounting stem 366B1 is also configured to couple with a cap 344A (FIG. 29). That is, mounting stem 366B1 can have the same configuration and alternatives as mounting stem 340, discussed above, and can securely engage with cap 344A in like manner. An elongated brace 362B2 likewise projects from back face 200B2 of mixing blade 176B along outside edge 288B2. Brace 362B2 has an outside face 364B2 facing away from mount 17B. A mounting stem 366B2 outwardly projects from outside face 364B2. Like mounting stem 366B1, mounting stem 366B2 is also configured to securely couple with a cap 344B.

Braces 362 provide structural support for blades 174 and 176 and also provide a structural surface on which to mount mounting stems 366. Braces 362 can also have some influence on mixing. Impeller segments 352A and 352C can also be formed with braces 362 to add symmetry and balance to impeller 350A. However, in other embodiments, braces 362 can be eliminated and mounting stems 366 can project directly from outside edge 208 of mixing blades 174B and 176B. In yet other embodiments, mounting stems 366B1 and 366B2 could be moved to or also be disposed on impeller segment 170A and/or 170C.

During assembly, impeller segments 352A-C are secured together a discussed above. As depicted in FIGS. 29 and 30, mounting stem 366B1 is passed through a hole 342 on drive member 334A and a cap 344A is secured to mounting stem 366B1. Likewise, mounting stem 366B2 is passed through a hole 342 on drive member 334B and a cap 344B is secured to mounting stem 366B2. As a result, impeller 350A is securely fixed to and between drive members 334A and 334B.

To help stabilize impeller 350A between drive members 334A and 334B, a stabilizer 370 can also be secured to and between drive members 334A and 334B and coupled with impeller 350A. Stabilizer 370 comprises a cross member 372 having a mounting stem 372A disposed at one end and a mounting stem 372B disposed at the opposing end. Mounting stems 372 are likewise configured to securely engage with caps 344A and B, respectively, and can have the same configurations and alternatives as mounting stems 340. A rod 376 centrally projects from cross member 372 and is configured to be received within passage 356 of impeller segment 352A and within openings 196 of impeller segments 352A-C (FIG. 31). Although not required, rod 376 typically has the same transverse cross section as passage 356 and openings 196.

During assembly, the free end of rod 376 is received within passage 356 and openings 196. Sleeve 354 functions to help support and retain rod 376 coupled to impeller segments 352A-C. Mounting stems 372A and 372B are passed through holes 342 on drive members 334A and 334B, respectively, and caps 344A and B are then secured thereon. As a result, stabilizer 370 is secured to and between drive members 334A and 334B and is coupled to impeller 350A. That is stabilizer 370 is secured to drive members 334A and 334B at a location relative to impeller 350A so that during operation, rod 376 cannot separate from impeller 350A. Rather, stabilizer 370 functions to limit twisting of impeller 350A so that impeller 350A is more stable for optimal mixing. Impellers 350B and 350C are likewise secured to and between drive members 334A and 334B at spaced apart locations using stabilizers 370. Any desired number of impellers 350 can be used depending on the application and mixing requirements.

Figure 33:
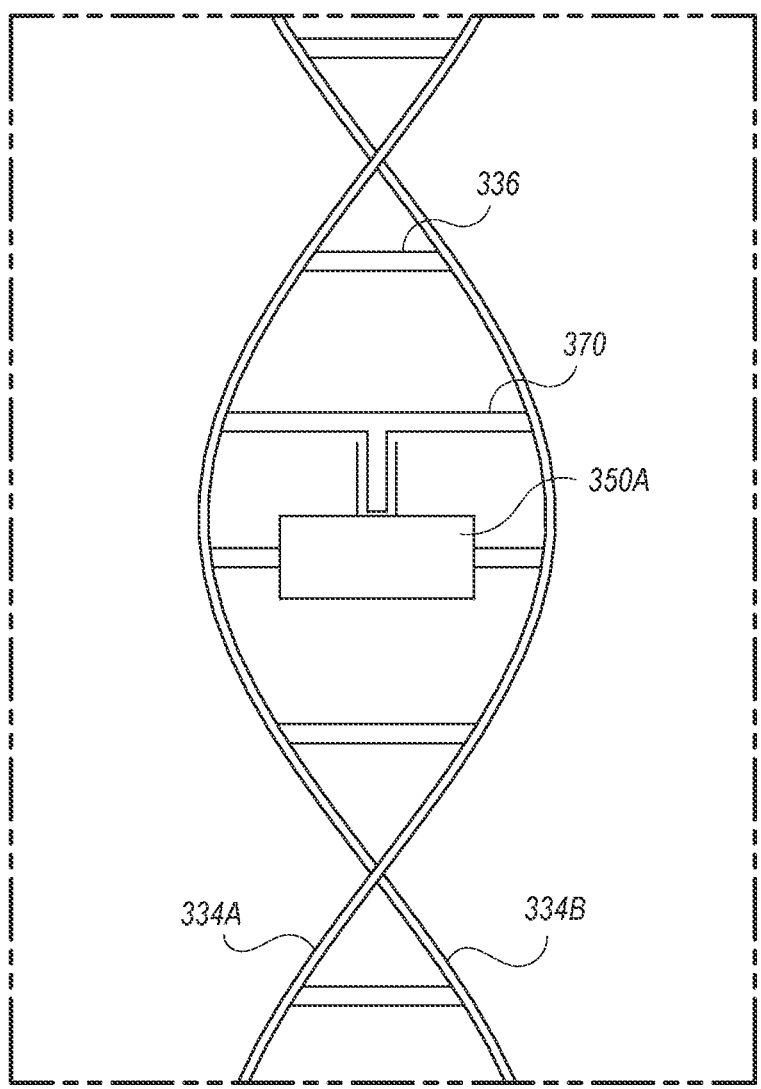
FIG. 33 is a schematic side view of a portion of the mixer assembly shown in FIG. 28 in a twisted helical configuration.

With reference to FIG. 26, drive members 334A and 334B are typically sized so that they can be slack when container 12 is disposed within support housing 300 and coupled with motor assembly 306. Because Drive members 334A and 334B are slack and made of a flexible material, drive members 334A and 334B will twist into a helical configuration along their length during operation (FIG. 33), i.e., drive members 334A and 334B form a double stranded helix. That is, the upper end of drive members 334A and 334B begin to rotate concurrently with the rotation of drive shaft 314 as driven by motor assembly 306. However, as a result of the resistance produced by the liquid on impellers 350, rungs 336, and other structures, drive members 334A and 334B begin to twist into the helical configuration during operation so as to cause each drive members 334A and 334B to come under torsion. In addition, as drive members 334A and 334B twist into the helical configuration, the vertical length drive members 334A and 334B is shorted. However, because the lower end of mixer assembly 302 is secured to the floor of support housing 300 by retaining post 322, the shortening of drive members 334A and 335B is limited. Once sufficient torsion is placed on drive members 334A and 335B to overcome the fluid resistance and friction force, the entire length of drive members 334A and 334B, and thus the entire length of mixer assembly 302, rotate within container 12. This rotation of impellers 350A-C helps to facilitate mixing and/or suspension of the liquid within container 12.

With reference to FIG. 28, during operation impellers 350A-C along with drive members 334A and 334B rotate about a rotational axis 396. It is again noted that impellers 350A-C are each typically assembled and secured to drive members 334A and 334B so that a plane 212 disposed perpendicular rotational axis 396 and passing through any of impellers 350A-C can intersect with all of the mixing blades 174 and 176 of the impeller. That is, in some of the embodiments, each of impellers segments 352 are disposed sufficiently close together so that mixing blades 174 and 176 work together to function as a single impeller.

Drive members 334A and 334B are, in part, specifically designed to twist into a helical configuration to minimize the tension and torsion force that drive members 334A and 334B are subject to during operation. That is, as drive members 334A and 334B twist into the helical configuration, as discussed above and depicted in FIG. 33, a portion of the torsion and tension that is applied to drive members 334A and 334B is converted to a vector force that tries to push members 334A and 334B together. This vector force is applied to the opposing ends of rungs 336 and impellers 350 which, as a result, places rungs 336 and impellers 350 under compression. Rungs 336 and impellers 350, however, are sufficiently rigid and have sufficient strength to carry the compressive load without failure and thus maintain the spacing between drive members 334A and 334B.

Drive members 334A and 334B are also an example of means secured to impeller segments for concurrently rotating the impeller segments about a rotational axis. Other examples of such means includes the alternatives and modifications to drive members 334A and 334B as disclosed or incorporated herein.

Further disclosure with regard to fluid mixing system 10B, including the components, assembly, use, and alternatives thereof, are disclosed in US Patent Publication No. 2017/0183617, published Jun. 29, 2017 and US Patent Publication No. 2019/0217261, published Jul. 18, 2019 which are incorporated herein in their entirety by specific reference.

Figure 34:
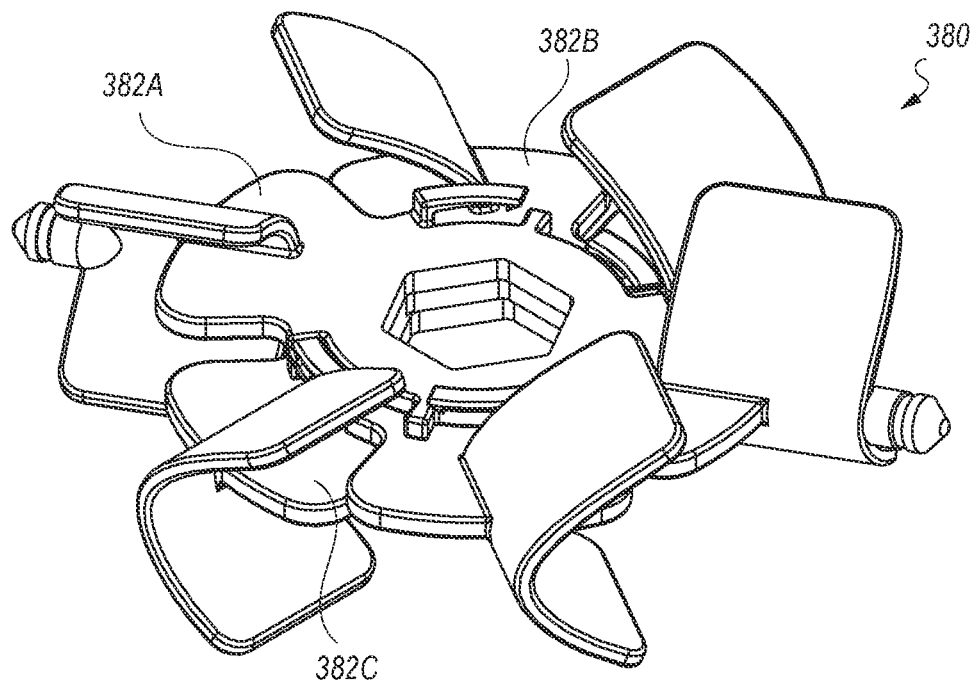
FIG. 34 is a perspective of an alternative embodiment of an impeller that can be used with the mixing system shown in FIG. 25.
Figure 35:
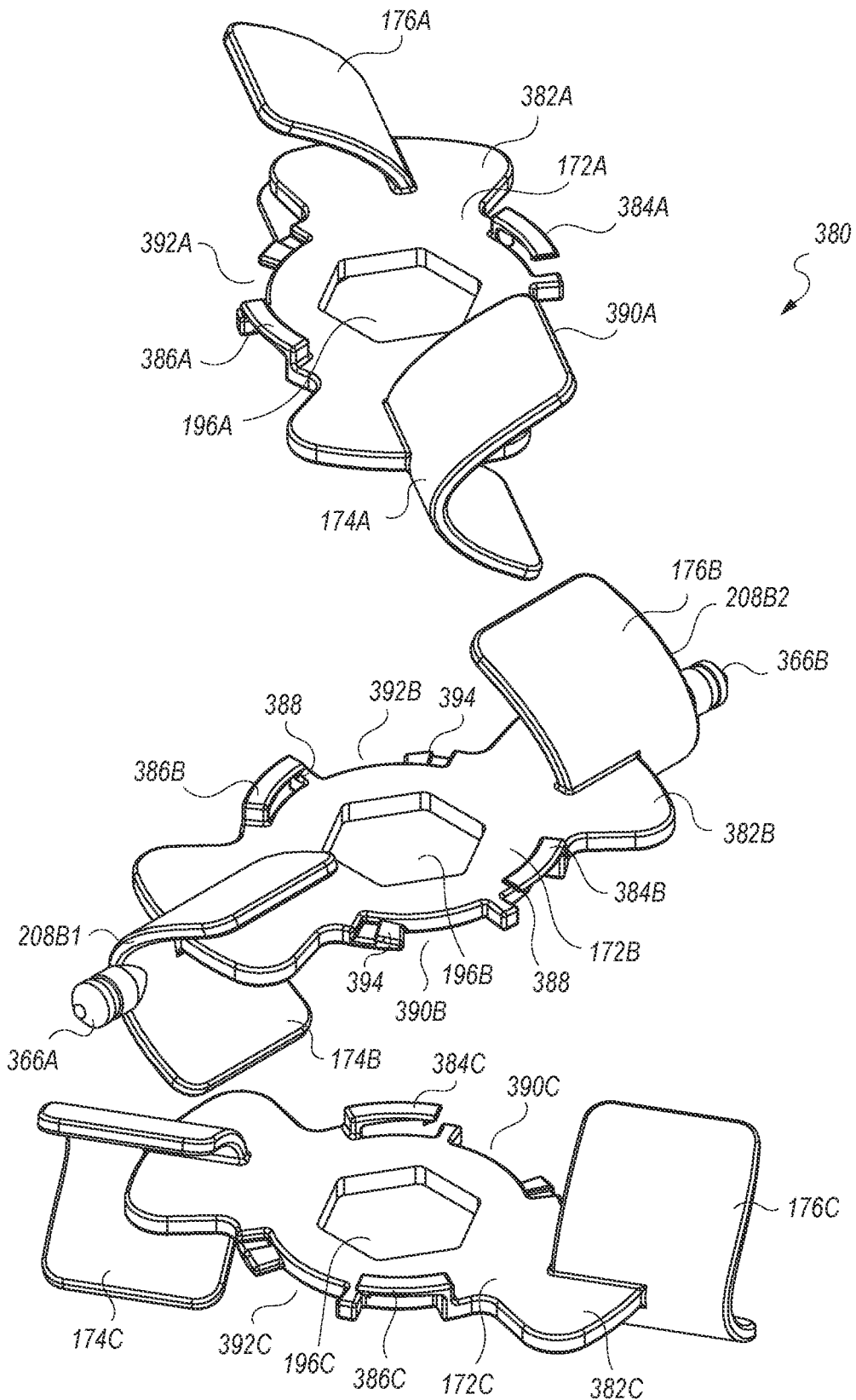
FIG. 35 is an exploded view of the impeller shown in FIG. 34.

It is appreciated that impellers 350 can have still other configurations. For example, depicted in FIGS. 34 and 35 is an example of an alternative impeller 380 having impeller segments 382A-C. Like elements between impeller 380 and the other impellers disclosed herein are identified by like reference numbers. Each impeller segment 382A-C also includes mount 172 having opening 196 extending therethrough and mixing blades 174 and 176 projecting from opposing ends of mount 172. As such, all of the previous discussion, elements, methods and alternatives relating to mounts 172 and mixing blades 174 and 176 of the other impellers disclosed herein are also applicable to impeller segments 382. Impeller segment 382B includes mounting stems 366A and B outwardly projecting from outside edges 208 of mixing blades 174B and 176B. Mounting stems 366 are configured to pass through holes 342 in drive members 334 and couple with caps 344 (FIG. 30). Impeller 380 can also couple with stabilizer 370 as discussed above with regard to impeller 350A. However, in contrast to having posts 358 and holes 360 for producing a press fit connection, impeller segments 382A-C are formed with hooks and catches for coupling impeller segments 382A-C together.

Specifically, impeller segment 382B has a pair of flexible arms 384B and 386B disposed on opposing sides of mount 172B. Each arm 384B and 386B has a hook 388 mounted on the end thereof. Complementary slots 390A and 392A are also formed on opposing sides of mount 172B and each have a catch 394 adjacently disposed. Impeller segments 382A and 382C likewise have corresponding arms 384 and 386 each with hook 388 and slots 390 and 392 each with catch 394. During assembly, arms 384C and 386C of impeller segment 382C are received within slots 390B and 392B of impeller segment 382B. Impeller segment 382B is then rotated relative to impeller segment 382C so that hooks 388 extend over catches 394 so as to secure impeller segment 382C to impeller segment 382B. Impeller segment 382B is likewise secured to impeller segment 382A, thereby resulting in impeller segments 382A-C being securely coupled together. Arms 384, 386 and slots 390, 390 with related hooks 388 and catches 394 are thus a further alternative embodiment of the means for securely fixing together impeller segments 382A-C.

It is again noted that the different features of the different impellers and impellers segments disclosed herein can be mixed and matched in any desired combination to achieve a desired configuration having desired properties. For example, posts 358 and holes 360 discussed above with regard to impellers 350 or hooks 388 and catches 394 (and related components) discussed above with regard to impeller 380 can also be used to assemble together any of the alternative impeller segments previously discussed above with regard to impeller 85. Likewise, any of the previously discussed alternative features associated with impeller 85 can also be incorporated into impellers 350 and 380.

The modular impellers disclosed herein have a number of unique advantages. For example, although not required, in one embodiment the modular impellers have curved mixing blades, e.g., have a concave or parabolic configuration, which improves mixing efficiency without increasing shear forces on liquid. However, by making the impellers out of two or more separate impeller segments that are coupled or disposed together, as opposed to being a single part, results in the impellers being relatively easy and inexpensive to mass produce by injection molding. That is, an impeller segment having only one or two mixing blades, even if parabolic, has a structure that is substantially less complex than an impeller having six parabolic blades. As such, a mold can be easily produced for injection molding the impeller segments from a polymer material. Other molding processes can also be used. Although not required, the manufacturing and assembly is further simplified where each or at least some of the impeller segments are identical. That is, by having identical impeller segments that can be grouped or coupled together to form an impeller, fewer molds are required and assembly is simplified.

Furthermore, by forming modular impellers from impeller segments each having one or more mixing blades thereon, the configuration, size, orientation, and/or type of mixing blades can be easily varied between different impeller segments forming an impeller. That is, by varying the impeller blades between different impeller segments, the mixing efficiency can be improved and/or the mixing properties, e.g., flow path, shear, turbulence, can be tailored to specific applications.

In addition, in some embodiments, the mixing blades on different impeller segments are slightly offset along the length of the rotational axis. Having the mixing blades slightly offset longitudinally has been found to improve the mixing efficiency.

Furthermore, forming an impeller from separate impeller segments also simplifies production by methods other than injection molding. For example, the multiple impeller segments can be printed faster and at a lower cost than a single impeller of corresponding structure. Specifically, forming separate impeller segments takes up less space in a printer, requires less support material during printing, and makes it easier to access and remove the support material.

Using multiple impeller segments to form an impeller also makes it easy to adjust the number of mixing blades that are used. That is, any desired number of mixing segments can be combined to achieve any desired number of mixing blades. This is especially true where the impeller segments all have the same configuration. Other benefits also exist.

Various alterations and/or modifications of the inventive features illustrated herein, and additional applications of the principles illustrated herein, which would occur to one skilled in the relevant art and having possession of this disclosure, can be made to the illustrated embodiments without departing from the spirit and scope of the invention as defined by the claims, and are to be considered within the scope of this disclosure. Thus, while various aspects and embodiments have been disclosed herein, other aspects and embodiments are contemplated. While a number of methods and components similar or equivalent to those described herein can be used to practice embodiments of the present disclosure, only certain components and methods are described herein.

It will also be appreciated that systems, processes, and/or products according to certain embodiments of the present disclosure may include, incorporate, or otherwise comprise properties features (e.g., components, members, elements, parts, and/or portions) described in other embodiments disclosed and/or described herein. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include said features without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative systems, processes, products, and the like are not described herein in particular detail in order to avoid obscuring aspects of the example embodiments. Such aspects are, however, also contemplated herein.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims. All changes which come within the meaning and range of equivalency of the claims are to be embraced within their scope.

What is claimed is:

1. A mixing system for mixing a liquid, comprising:
a first impeller segment comprising a first mount and a first mixing blade of the first impeller segment secured to the first mount;
a second impeller segment comprising a second mount and a first mixing blade of the second impeller segment secured to the second mount, the second impeller segment being separate and discrete from the first impeller segment;
a third impeller segment comprising a third mount and a first mixing blade of the third impeller segment, the third impeller segment being separate and discrete from the first impeller segment and the second impeller segment; and
means secured directly to the mount of the first impeller segment, the mount of the second impeller segment, and the mount of the third impeller segment for concurrently rotating the first impeller segment, the second impeller segment, and the third impeller segment about a rotational axis,
wherein the first impeller segment, the second impeller segment, and the third impeller segment are secured to the means for concurrently rotating so that a plane extending normal to the rotational axis intersects with the first mixing blade of the first impeller segment, the first mixing blade of the second impeller segment, and the first mixing blade of the third impeller segment,
wherein the first mount, the second mount, and the third mount each comprise an opening through which the rotational means passes.

2. The mixing system as recited in claim 1, further comprising a second mixing blade of the first impeller segment secured to the first mount and being spaced apart from the first mixing blade of the first impeller segment.

3. The mixing system as recited in claim 2, wherein the first mixing blade of the first impeller segment and the second mixing blade of the first impeller segment are the only mixing blades secured to the first mount of the first impeller segment.

4. The mixing system as recited in claim 1, wherein the first impeller segment and the second impeller segment have identical configurations.

5. The mixing system as recited in claim 1, wherein the openings of the first mount and the second mount are aligned.

6. The mixing system as recited in claim 1, wherein the first mount has a top face and an opposing bottom face and the second mount has a top face and an opposing bottom face, the bottom face of the first mount being disposed directly against or directly adjacent to the top face of the second mount.

7. The mixing system as recited in claim 1, wherein the first mount and the second mount are disposed at different locations along the rotational axis.

8. The mixing system as recited in claim 1, wherein the plane extending normal to the rotational axis does not intersect with both the first mount and the second mount.

9. The mixing system as recited in claim 1, wherein the first mixing blade of the first impeller segment has a front face with a concave or parabolic configuration.

10. The mixing system as recited in claim 1, wherein the first mixing blade of the first impeller segment further comprises a front face and an opposing back face, the front face having a length that extends from a first terminal end to an opposing second terminal end and having a width that extends between an inside edge connected to the first mount and an opposing outside edge.

11. The mixing system as recited in claim 10, wherein at least a portion of the front face of the first mixing blade of the first impeller segment extends linearly between the inside edge and the opposing outside edge.

12. The mixing system as recited in claim 1, further comprising means for securing the first impeller segment to the second impeller segment.

13. The mixing system as recited in claim 1, wherein the means for concurrently rotating comprises a first drive member coupled to the first impeller segment and the second impeller segment.

14. The mixing system as recited in claim 13, wherein the first drive member is disposed within the opening of the first mount and the opening of the second mount.

15. The mixing system as recited in claim 13, wherein the first drive member is tubular, a drive shaft being removably received within the first drive member.

16. The mixing system as recited in claim 1, wherein the means for concurrently rotating comprises a first drive member secured to the second impeller segment and a second drive member secured to the second impeller segment.

17. A mixing system for mixing a liquid, comprising:
a first impeller segment comprising a first mount, a first mixing blade of the first impeller segment secured to the first mount, and a second mixing blade of the first impeller segment secured to the first mount, the first mixing blade of the first impeller segment being spaced apart from the second mixing blade of the first impeller segment;
a second impeller segment comprising a second mount and a first mixing blade of the second impeller segment secured to the second mount, the second impeller segment being separate and discrete from the first impeller segment;
a third impeller segment comprising a third mount and a first mixing blade of the third impeller segment, the third impeller segment being separate and discrete from the first impeller segment and the second impeller segment; and
an elongated first drive member, the mount of the first impeller segment, the mount of the second impeller segment, and the mount of the third impeller segment being secured directly to the first drive member such that a plane intersects with the first mixing blade of the first impeller segment, the second mixing blade of the first impeller segment and also with the first mixing blade of the second impeller segment, and the first mixing blade of the third impeller segment,
wherein the first mount, the second mount, and the third mount each comprise an opening through which the elongated first drive member passes.

18. The mixing system as recited in claim 17, wherein the first mixing blade of the first impeller segment has a front face with a concave or parabolic configuration.

19. A mixing system for mixing a liquid, comprising:
a first impeller segment comprising a first mount and only two mixing blades or only one mixing blade being secured to the first mount;
a second impeller segment comprising a second mount and only two mixing blades or only one mixing blade being secured to the second mount, the second impeller segment being separate and discrete from the first impeller segment;
a third impeller segment comprising a third mount and only two mixing blades or only one mixing blade being secured to the third mount, the third impeller segment being separate and discrete from the first impeller segment and the second impeller segment;
an elongated first drive member directly secured to the mount of the first impeller segment and/or the mount of the second impeller segment and/or the mount of the third impeller segment; and a collapsible, flexible bag having a compartment and being comprised of one or more sheets of polymeric film, the first impeller segment, the second impeller segment, the third impeller segment, and at least a portion of the elongated first drive member being disposed within the compartment of the flexible bag, wherein the first mount, the second mount, and the third mount each comprise an opening through which the elongated first drive member passes.

* * * * *